US012683007B2

(12) United States Patent
Kandur Raja et al.

(10) Patent No.: US 12,683,007 B2
(45) Date of Patent: Jul. 14, 2026

(54) METHOD AND ELECTRONIC DEVICE FOR PREDICTING EMOTION OF USER

(71) Applicant: SAMSUNG ELECTRONICS CO., LTD., Suwon-si (KR)

(72) Inventors: Barath Raj Kandur Raja, Bengaluru (IN); Sumit Kumar, Bengaluru (IN); Sriram Shashank, Bengaluru (IN); Harichandana Bhogaraju Sawaraja Sai, Bengaluru (IN); Chinmay Anand, Bengaluru (IN); Jayesh Rajkumar Vachhani, Bengaluru (IN); Ankita Bhardwaj, Bengaluru (IN); Shwetank Choudhary, Bengaluru (IN); Srishti Malaviya, Bengaluru (IN); Tarun Gopalakrishnan, Bengaluru (IN); Dwaraka Bhamidipati Sreevatsa, Bengaluru (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 210 days.

(21) Appl. No.: 18/228,455

(22) Filed: Jul. 31, 2023

(65) Prior Publication Data

US 2023/0377717 A1 Nov. 23, 2023

Related U.S. Application Data

(63) Continuation of application No. PCT/KR2023/006130, filed on May 4, 2023.

(30) Foreign Application Priority Data

May 4, 2022 (IN) .............................. 202241026033
Apr. 26, 2023 (IN) .............................. 202241026033

(51) Int. Cl.
*G16H 20/70* (2018.01)
*G06F 11/34* (2006.01)

(52) U.S. Cl.
CPC ......... *G16H 20/70* (2018.01); *G06F 11/3438* (2013.01)

(58) Field of Classification Search
CPC ...................................................... G16H 20/70
See application file for complete search history.

(56) References Cited

U.S. PATENT DOCUMENTS 8,341,109 B2   12/2012   Sim et al.
8,683,348 B1 *   3/2014   Blank ..................... G06F 3/038
                                                                            715/709
(Continued)

FOREIGN PATENT DOCUMENTS

CN       110785762 A       2/2020
EP       3 820 369 A0       4/2020
(Continued)

OTHER PUBLICATIONS

Shapsough et al., "Emotion Recognition Using Mobile Phones", 2016 IEEE 18th International Conference on e-Health Networking, Applications and Services (Healthcom) (Year: 2016).*

(Continued)

*Primary Examiner* — Anne-Marie K Alderson
(74) *Attorney, Agent, or Firm* — Sughrue Mion, PLLC

(57) ABSTRACT

Provided is a method for predicting emotion of a user by an electronic device. The method includes receiving, by the electronic device, a user context, a device context and an environment context from the electronic device and one or more other electronic device connected to the electronic device and determining, by the electronic device, a combined representation of the user context, the device context and the environment context. The method also includes (Continued)

determining, by the electronic device, a plurality of user characteristics based on the combined representation of the user context, the device context and the environment context; and predicting, by the electronic device, an emotion of the user based on the combined representation of the user context, the device context, the environment context and the plurality of user characteristics.

16 Claims, 27 Drawing Sheets

(56) References Cited

U.S. PATENT DOCUMENTS

| | | | |
|---|---|---|---|
| 9,299,268 | B2 | 3/2016 | Aravkin et al. |
| 10,326,667 | B2 | 6/2019 | Jones et al. |
| 10,368,120 | B2 | 7/2019 | Mattingly et al. |
| 10,552,004 | B2 | 2/2020 | Hu et al. |
| 10,922,490 | B2 | 2/2021 | Jain |
| 10,963,774 | B2 | 3/2021 | Osotio et al. |
| 11,113,719 | B2 | 9/2021 | Weldemariam et al. |
| 2006/0074883 | A1 | 4/2006 | Teevan et al. |
| 2009/0140864 | A1* | 6/2009 | Aaron .................... G06Q 30/02 |
| | | | 700/90 |
| 2010/0228696 | A1 | 9/2010 | Sim et al. |
| 2013/0018837 | A1 | 1/2013 | Lee |
| 2013/0086519 | A1 | 4/2013 | Fino |
| 2014/0089399 | A1 | 3/2014 | Chun et al. |
| 2014/0101296 | A1 | 4/2014 | Li et al. |
| 2014/0207811 | A1 | 7/2014 | Kim et al. |
| 2016/0302711 | A1 | 10/2016 | Frank et al. |
| 2018/0101579 | A1* | 4/2018 | Jaiswal .................. G06F 9/451 |
| 2018/0121784 | A1* | 5/2018 | Ichiboshi ............... G16H 10/20 |
| 2019/0239791 | A1* | 8/2019 | Beck ...................... A61B 5/163 |
| 2019/0266999 | A1* | 8/2019 | Chandrasekaran ..... G06F 3/167 |
| 2020/0026957 | A1 | 1/2020 | Jin et al. |
| 2020/0321002 | A1* | 10/2020 | Shin ....................... G06N 3/049 |
| 2021/0011614 | A1* | 1/2021 | Gustman ............. G06F 3/04847 |
| 2021/0149492 | A1 | 5/2021 | Dobson |
| 2021/0166816 | A1* | 6/2021 | Khan ................. G06Q 10/1093 |
| 2022/0028157 | A1 | 1/2022 | Gabral et al. |
| 2022/0223064 | A1 | 7/2022 | Chauhan et al. |
| 2022/0304603 | A1* | 9/2022 | Freckleton ............. G16H 50/20 |
| 2025/0006354 | A1* | 1/2025 | Larcher ................. G16H 10/20 |

FOREIGN PATENT DOCUMENTS

| | | |
|---|---|---|
| KR | 10-2010-0100380 A | 9/2010 |
| KR | 10-2012-0030396 A | 3/2012 |
| KR | 10-1349285 B1 | 1/2014 |
| WO | 2017/043857 A1 | 3/2017 |
| WO | 2018/128794 A1 | 7/2018 |
| WO | 2019/157633 A1 | 8/2019 |

OTHER PUBLICATIONS

Kolakowska et al., A Review of Emotion Recognition Methods Based on Data Acquired via Smartphone Sensors, 2020, Sensors 20(21), 6367 (Year: 2020).*

Duan et al., "Metaverse for Social Good: A University Campus Prototype," arXiv:2108.08985v1 [cs.MM], Aug. 2021, Total 9 pages.

Fugate et al., "What Color Is Your Anger? Assessing Color-Emotion Pairings in English Speakers," Frontiers in Psychology, vol. 10, Article 206, Feb. 2019, Total 17 pages.

Kurt et al., "The Effects of Color on the Moods of College Students," SAGE Open, Jan.-Mar. 2014, Total 12 pages.

Likamwa et al., "MoodScope: Building a Mood Sensor from Smartphone Usage Patterns," MobiSys'13, Jun. 2013, Total 14 pages.

Sarsenbayeva et al., "Does Smartphone Use Drive our Emotions or vice versa? A Causal Analysis," CHI 2020 Paper, Apr. 2020, Total 15 pages.

Adebayo, "Nemesysco spinoff unveils emotional detection and AI tools for metaverse," VentureBeat, Mar. 28, 2022, Total 10 pages, retrieved from https://venturebeat.com/2022/03/28/nemesysco-spinoff-unveils-emotional-detection-and-ai-tools-for-metaverse/.

TechGig, "This Japanese firm is working on filling emotions in your metaverse self," Mar. 27, 2022, Total 18 pages, retrieved from https://content.techgig.com/technology-unplugged/this-japanese-firm-is-working-on-filling-emotions-in-your-metaverse-self/articleshow/90466777.cms.

Moody et al., "An Exploratory study: Relationships between Trying on Clothing, Mood, Emotion, Personality and Clothing Preference," Journal of Fashion Marketing and Management, vol. 14, No. 1, University of Huddersfield Repository, 2010, Total 24 pages.

Clabum, "This is going well: Meta adds anti-grope buffer zone around metaverse VR avatars," Personal Tech, Feb. 5, 2022, Total 6 pages, retrieved from https://www.theregister.com/2022/02/05/meta_grope_gap/.

Search Report and Written Opinion (PCT/ISA/210, and PCT/ISA/237) dated Aug. 10, 2023, issued by the ISA for International Application No. PCT/KR2023/006130.

Rafael Wampfler et al., "Affective State Prediction from Smartphone Touch and Sensor Data in the Wild", CHI '22: Proceedings of the 2022 CHI Conference on Human Factors in Computing Systems, Article No. 403, Apr. 2022, pp. 1-14, DOI: 10.1145/3491102.3501835, XP059727269.

Communication issued on Feb. 25, 2025 from the European Patent Office in European Patent Application No. 23799709.3.

* cited by examiner

FIG. 2

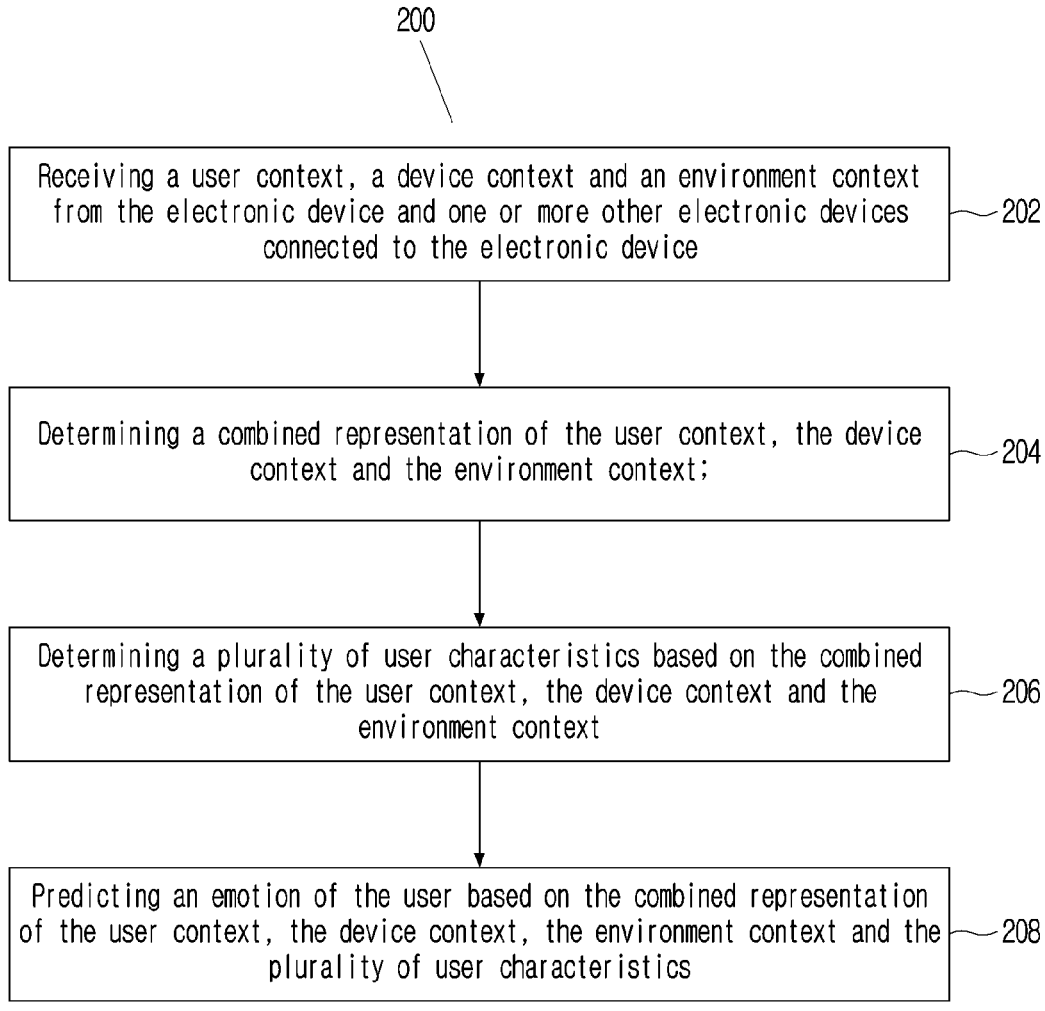

200

Receiving a user context, a device context and an environment context from the electronic device and one or more other electronic devices connected to the electronic device ——202

Determining a combined representation of the user context, the device context and the environment context; ——204

Determining a plurality of user characteristics based on the combined representation of the user context, the device context and the environment context ——206

Predicting an emotion of the user based on the combined representation of the user context, the device context, the environment context and the plurality of user characteristics ——208

FIG. 3

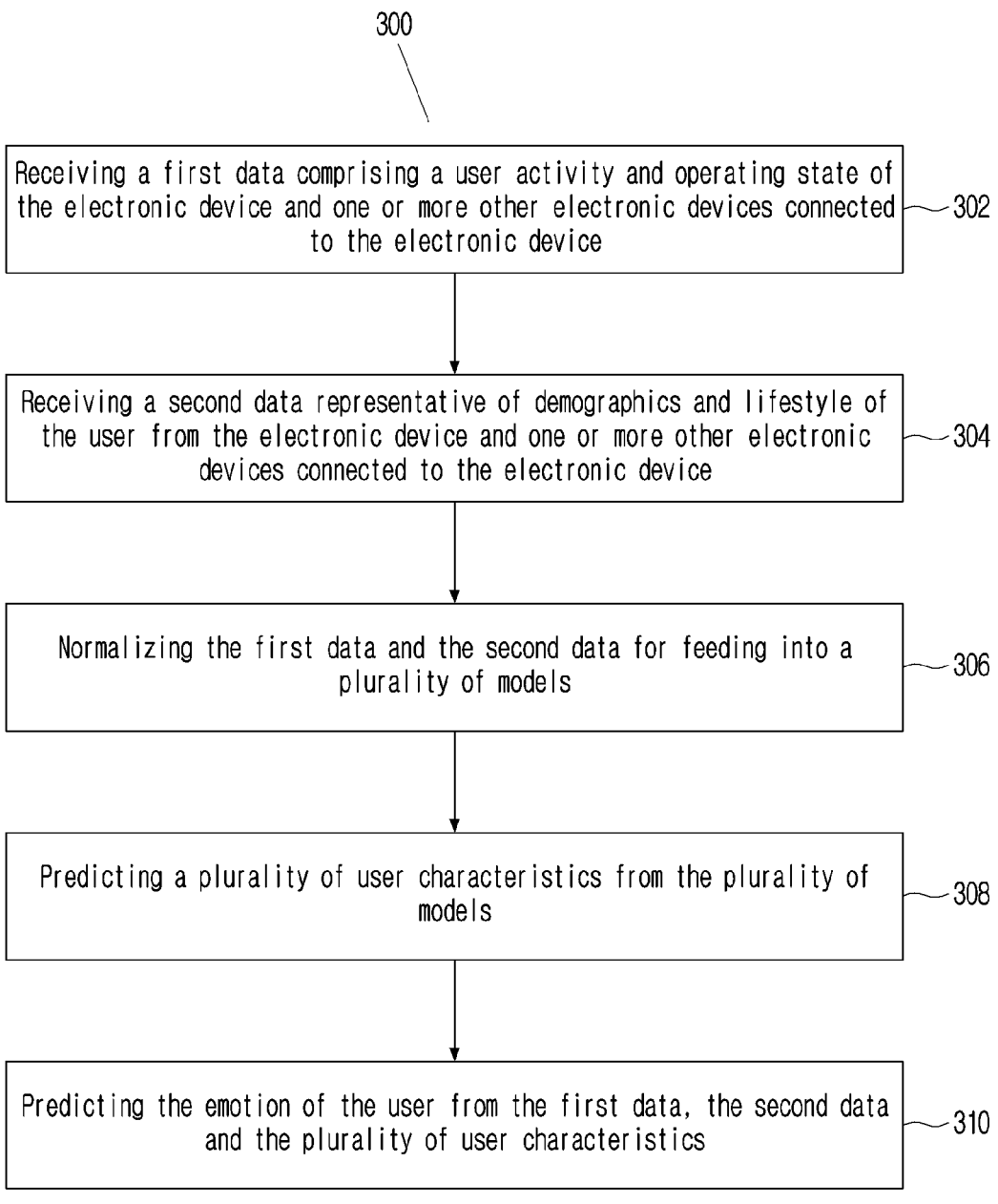

300

Receiving a first data comprising a user activity and operating state of the electronic device and one or more other electronic devices connected to the electronic device — 302

Receiving a second data representative of demographics and lifestyle of the user from the electronic device and one or more other electronic devices connected to the electronic device — 304

Normalizing the first data and the second data for feeding into a plurality of models — 306

Predicting a plurality of user characteristics from the plurality of models — 308

Predicting the emotion of the user from the first data, the second data and the plurality of user characteristics — 310

1401

100

Your emotions

This month you were happy!

☺ Happy                          29%
♡ Affectionate                   13%
☹ Stressed                        7%

Your apps
Samsung Health                    ☺
Calender                          ☹

Your friends
Ⓜ Mom                            ☺
Ⓜ Matthew                        ♡

1402

100 abhil                            ×

🔍 Abhiji

Contacts 7          Search in app
Ⓐ Abhi Mama
Ⓐ Abhijit Baruah
Ⓐ Abhijith            ♡ ☺
Show more Ⓖ Search with Google < Abhijith  Abhijit  Abhijieet ···
1 2 3 4 5 6 7 8 9 0
q w e r t y u i o p
a s d f g h j k l
⬆ z x c v b n m ⌫
!#1 , ⎵ . ↵

FIG. 15A
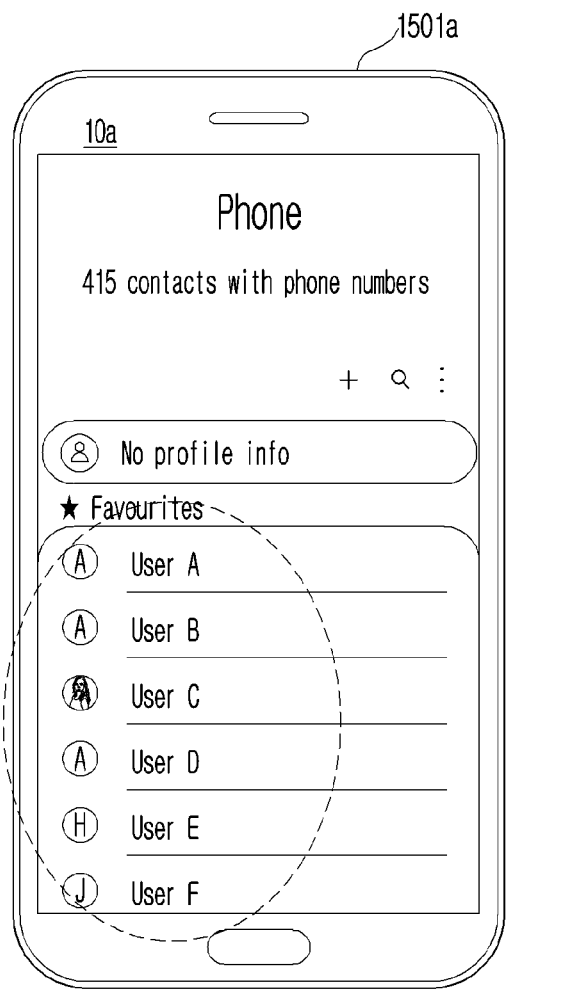
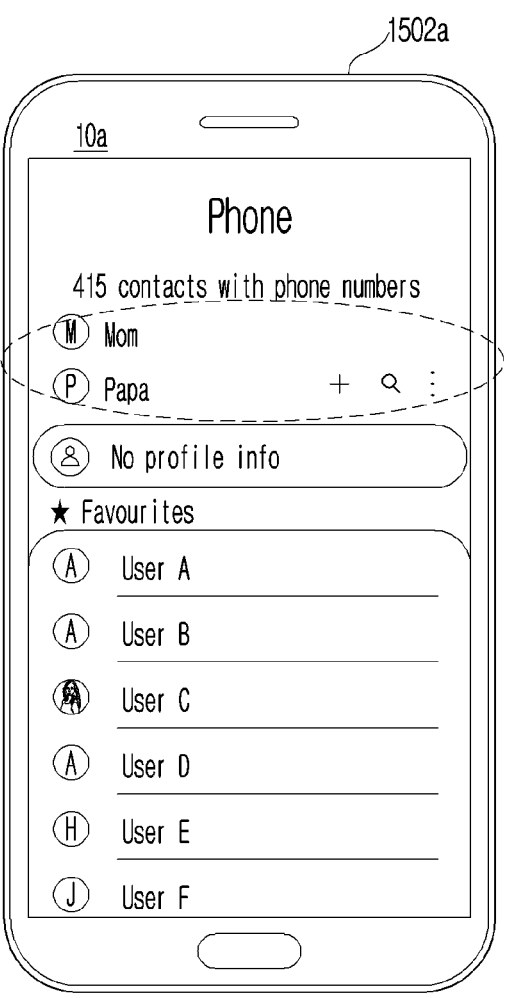

FIG. 15B
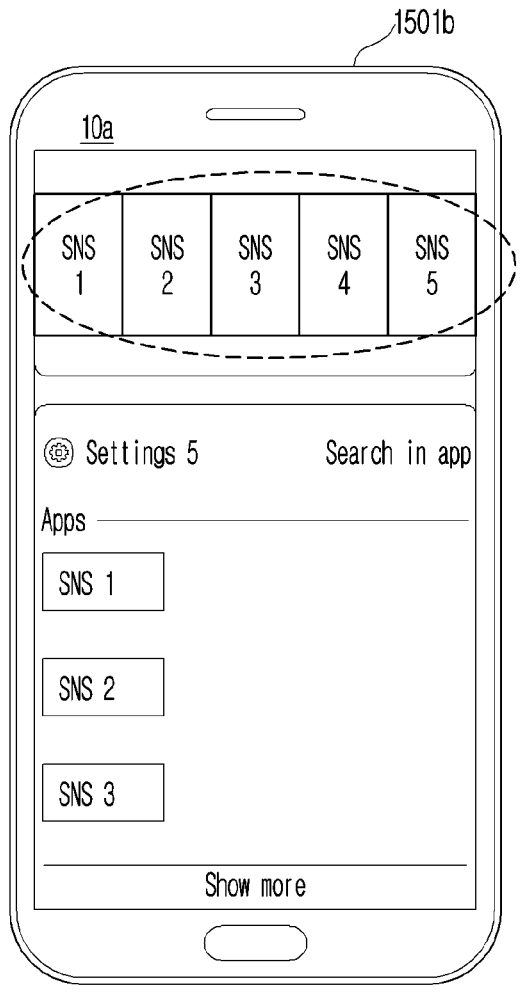
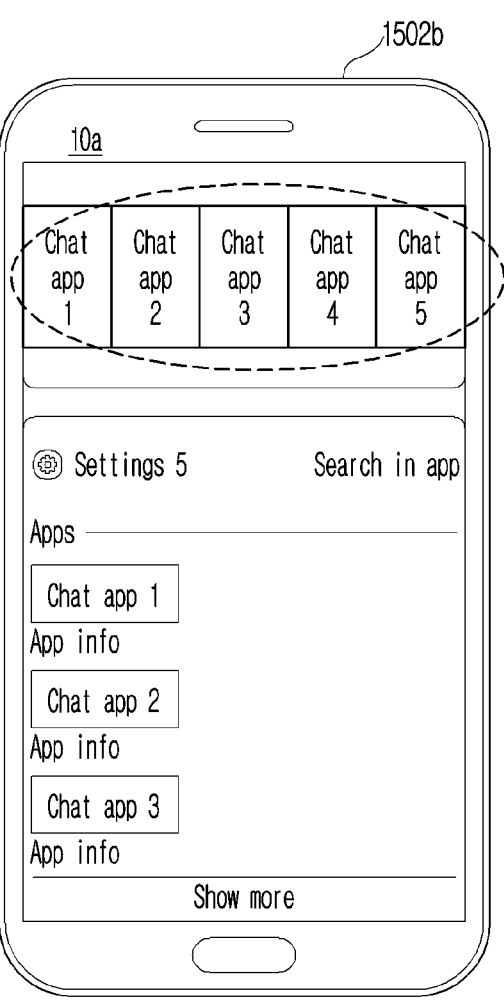

FIG. 15C
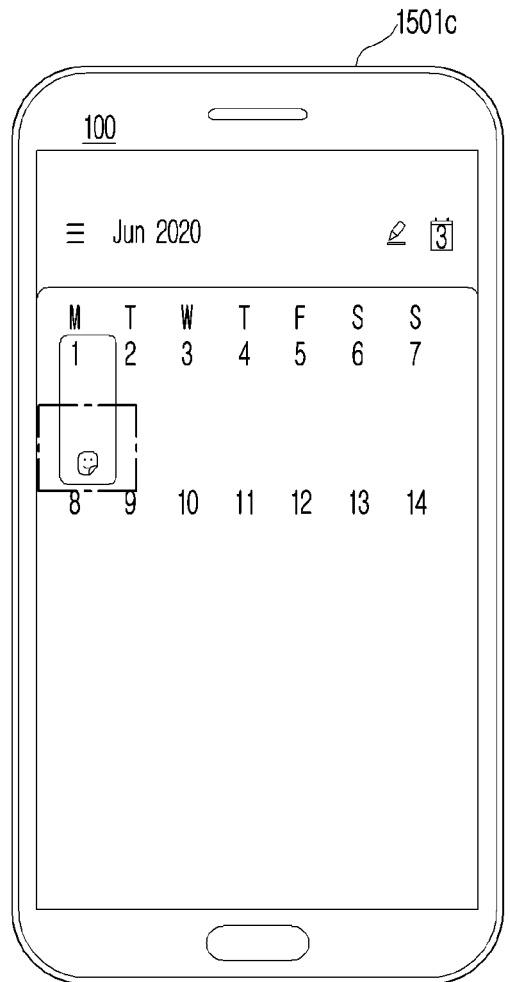
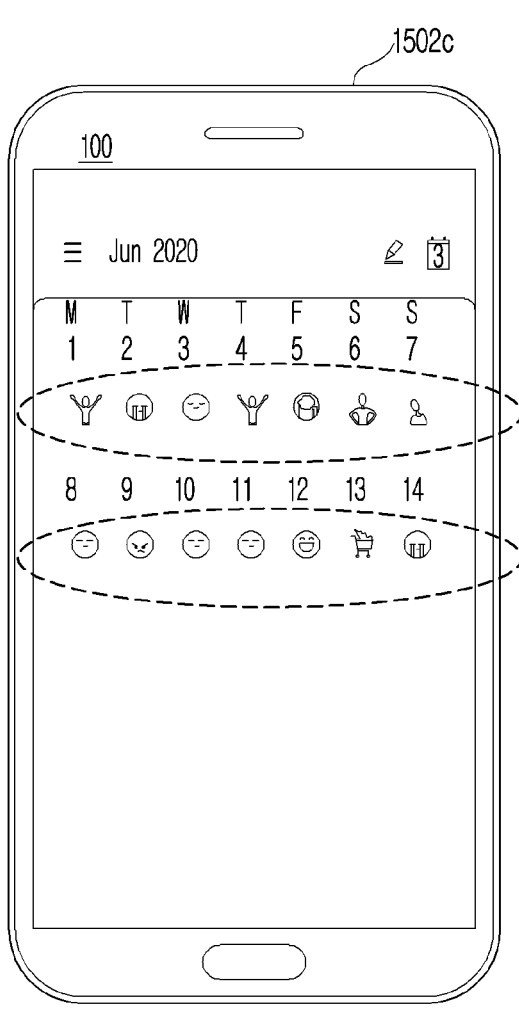

FIG. 15D
1501d
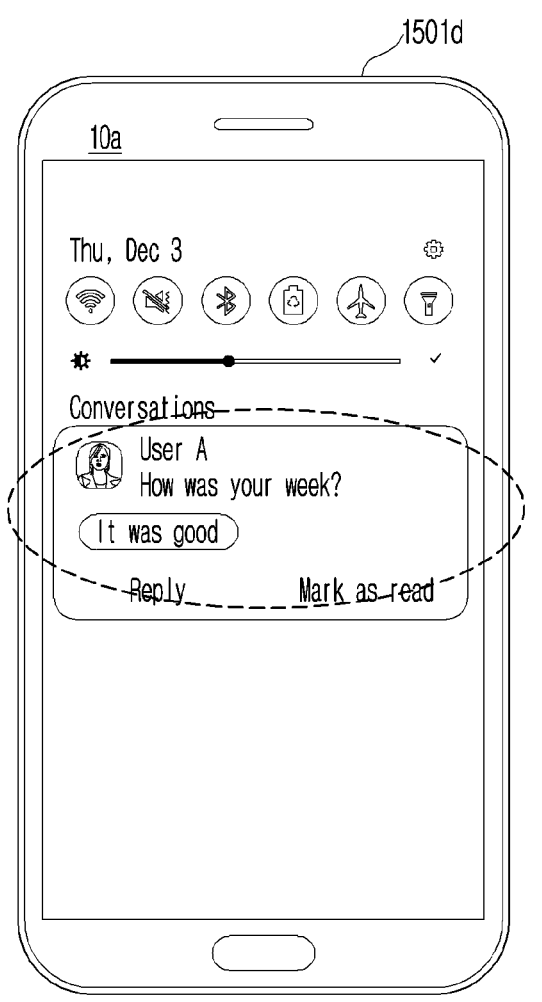
1502d
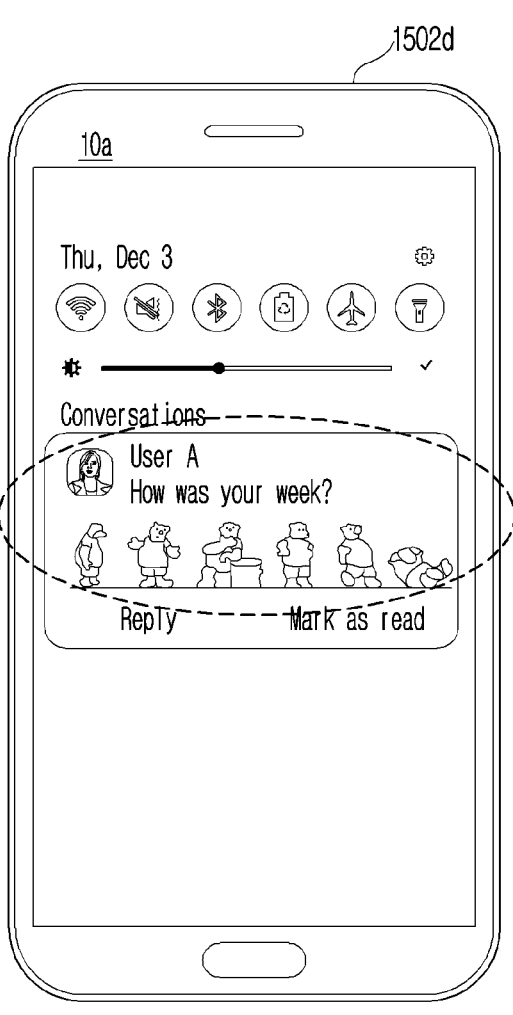

Anxiety      Sad      Happy      Disgust      Angry

METHOD AND ELECTRONIC DEVICE FOR PREDICTING EMOTION OF USER

CROSS-REFERENCE TO RELATED APPLICATIONS

This application is a by-pass continuation of PCT/KR2023/006130, filed on May 4, 2023, which is based on and claims priority to Indian Patent Application No. 202241026033, filed on May 4, 2022 in the Indian Patent Office, and to Indian Patent Application No. 202241026033, filed on Apr. 26, 2023 in the Indian Patent Office, the disclosures of all of which are incorporated by reference herein in their entireties.

BACKGROUND

1. Field

The disclosure relates to electronic devices, and more specifically relates to a method and an electronic device for predicting emotion of a user. The present application is based on and claims priority from an Indian Provisional Application Number 202241026033 filed on May 4, 2022, the disclosure of which is hereby incorporated by reference herein.

2. Description of Related Art

With advancement in technology, electronic devices have become an apparent part of human lives. A user of an electronic device is generally static but an emotional state of the user may be dynamic. However, the emotional state of the user needs to be taken into consideration for providing better user experience to the user of the electronic device.

Various existing methods for user activities such as, for example, conversations between chat bots and the user, are mechanical in nature with low personalization. Existing methods determine an emotional state of the user based on modalities such as, for example, text, voice, image, etc.; user actions such as for example, avatars personification and user's rating (UI), which may not provide an accurate emotional state of the user.

In virtual environments and applications, user personality and emotional state are not reflected appropriately in real time, which does not provide a comprehensive representation of the user. Various existing methods for determining the emotional state of the user do not consider dynamic factors such as user environment, and hence conversational applications such as chat bots, avatars, etc. provide similar responses irrespective of the emotional state of the user. Thus, it is desired to at least provide a mechanism devoid of the above issues.

SUMMARY

Provided is a method and electronic device for predicting emotion of a user by an electronic device. The proposed method predicts the emotion of the user based on various dynamic parameters including, but not limited to, data associated with the electronic device and a life pattern of the user using various models across multiple devices of the user. Therefore, unlike to the conventional methods and system, in the proposed method the predicted emotion can be used to dynamically vary options provided to the user based on the emotion of the user. As a result, the proposed method enhances user experience and provides personalization of the electronic device and various functions based on the emotions of the user.

Provided is a method for predicting emotion of a user by an electronic device. According to an aspect of the disclosure, a method for predicting an emotion of a user by an electronic device includes: receiving, by the electronic device, a user context, a device context and an environment context, wherein the user context, the device context, and the environment context are collected by at least one of the electronic device and at least one of one or more other electronic devices connected to the electronic device; determining, by the electronic device, a combined representation of the user context, the device context and the environment context; determining, by the electronic device, a plurality of user characteristics based on the combined representation of the user context, the device context and the environment context; and predicting, by the electronic device, the emotion of the user based on the plurality of user characteristics and the combined representation of the user context, the device context, the environment context.

The method for predicting emotion of a user by an electronic device may further include: performing, by the electronic device, based on the predicted emotion of the user, at least one of: modifying a user experience on the electronic device and on at least one of the one or more other electronic devices, personalizing content on the electronic device and on at least one of the one or more other electronic devices, utilizing an emotional profile on the electronic device and on at least one of the one or more other electronic devices, generating at least one object for providing an emotional support to the user, providing a security function to the user in a virtual environment, and modifying at least one user parameter in the virtual environment.

The method for predicting emotion of a user by an electronic device may further include: determining, by the electronic device, at least one of: a consumption of content by the user, abnormal usage pattern on the electronic device or on at least one of the one or more other electronic devices, a recurrence activity performed on the electronic device or on at least one of the one or more other electronic devices by the user, and a time duration spent by the user on the electronic device or on at least one of the one or more other electronic devices; and determining, by the electronic device, a quality of the predicted emotion of the user, wherein the quality of the predicted emotion is a positive emotion or a negative emotion.

The determining, by the electronic device, the plurality of user characteristics based on the combined representation of the user context, the device context and the environment context may include: providing, by the electronic device, the combined representation of the user context, the device context and the environment context to a first network and a plurality of intermediate models; and determining, by the electronic device, the plurality of user characteristics.

The method for predicting emotion of a user by an electronic device may further include: predicting, by the electronic device, a first set of intermediate emotions based on the plurality of user characteristics and the combined representation of the user context, the device context and the environment context.

The method for predicting emotion of a user by an electronic device may further include: providing, by the electronic device, the combined representation of the user context, the device context and the environment context to a second network and a third network; determining, by the electronic device, a local graph emotion prediction from the second network and a global node prediction from the third network; combining, by the electronic device, the local graph emotion prediction and the global node prediction based on a specific weight; and predicting, by the electronic device, a second set of intermediate emotions.

The determining, by the electronic device, the combined representation of the user context, the device context and the environment context may include: determining, by the electronic device, a plurality of features associated with the user from the user context, the device context and the environment context; segregating, by the electronic device, the plurality of features associated with the user into a plurality of categories corresponding to a specific duration of time; generating, by the electronic device using encoding, at least one vector representation for each of the plurality of categories; and determining, by the electronic device, the combined representation of the user context, the device context and the environment context based on the at least one vector representation for each of the plurality of categories.

The predicting, by the electronic device, the emotion of the user based on the combined representation of the user context, the device context, the environment context and the plurality of user characteristics may include: receiving, by at least one second model of the electronic device, a first set of intermediate emotions and a second set of intermediate emotions; receiving, by the at least one second model of the electronic device, a categorical clustering map; performing, by the at least one second model of the electronic device, an ensembling technique on the first set of intermediate emotions and the second set of intermediate emotions based on the categorical clustering map; and predicting, by the electronic device, the emotion of the user.

The plurality of user characteristics may be determined using at least one first model and the emotion of the user may be predicted using at least one second model.

According to an aspect of the disclosure, a method for predicting an emotion of a user by an electronic device includes: receiving, by the electronic device, first data comprising a user activity, an operating state of the electronic device, and an operating state of at least one of one or more other electronic devices connected to the electronic device; receiving, by the electronic device, second data representative of demographics and lifestyle of the user, wherein the second data is collected from at least one of the electronic device and at least one of the one or more other electronic devices connected to the electronic device; normalizing, by the electronic device, the first data and the second data for input into a plurality of models; predicting, by the electronic device, a plurality of user characteristics from the models; and predicting, by the electronic device, the emotion of the user based on the first data, the second data, and the plurality of user characteristics.

According to an aspect of the disclosure, an electronic device for predicting an emotion of a user includes: at least one memory configured to store at least one instruction; at least one processor in communication with the at least one memory; and a communicator in communication with the at least one memory the at least one processor, wherein the at least one processor is configured to execute the at least one instruction to: receive a user context, a device context and an environment context, wherein the user context, the device context, and the environment context are collected by at least one of the electronic device and at least one of one or more other electronic devices connected to the electronic device; determine a combined representation of the user context, the device context and the environment context;

determine a plurality of user characteristics based on the combined representation of the user context, the device context and the environment context; and predict the emotion of the user based on the plurality of user characteristics and the combined representation of the user context, the device context, the environment context.

The at least one processor of the electronic device may be further configured to execute the at least one instruction to: perform, based on the predicted emotion of the user, at least one of: modifying a user experience on the electronic device and on at least one of the one or more other electronic devices, personalizing content on the electronic device and on at least one of the one or more other electronic devices, utilizing an emotional profile on the electronic device and on at least one of the one or more other electronic devices, generating at least one object for providing an emotional support to the user, providing a security function to the user in a virtual environment; and modifying at least one user parameter in the virtual environment.

The at least one processor of the electronic device may be further configured to execute the at least one instruction to: determine at least one of: a consumption of content by the user, abnormal usage pattern on the electronic device or on at least one of the one or more other electronic devices, a recurrence activity performed on the electronic device or on at least one of the one or more other electronic devices by the user, and a time duration spent by the user on the electronic device or on at least one of the one or more other electronic devices; and determine a quality of the predicted emotion of the user, wherein the quality of the predicted emotion is a positive emotion or a negative emotion.

The at least one processor of the electronic device may be further configured to execute the at least one instruction to: determine the plurality of user characteristics based on the combined representation of the user context, the device context and the environment context by providing the combined representation of the user context, the device context and the environment context to a first network and a plurality of intermediate models.

The at least one processor of the electronic device may be further configured to execute the at least one instruction to: determine a combined representation of the user context, the device context and the environment context by: determining a plurality of features associated with the user from the user context, the device context and the environment context, segregating the plurality of features associated with the user into a plurality of categories corresponding to a specific duration of time, generating at least one vector representation for each of the plurality of categories, and determining the combined representation of the user context, the device context and the environment context based on the at least one vector representation for each of the plurality of categories.

The electronic device of claim 15, wherein the at least one processor is further configured to execute the at least one instruction to: predict the emotion of the user based on the plurality of user characteristics and the combined representation of the user context, the device context, the environment context by: receiving, by at least one second model of the electronic device, a first set of intermediate emotions and a second set of intermediate emotions; receiving, by the at least one second model of the electronic device, a categorical clustering map; performing, by the at least one second model of the electronic device, an ensembling technique on the first set of intermediate emotions and the second set of intermediate emotions based on the categorical clustering map; and predicting, by the electronic device, the emotion of the user.

The at least one processor of the electronic device may be further configured to execute the at least one instruction to: determine a plurality of user characteristics based on the combined representation of the user context, the device context and the environment context using at least one first model, and predict the emotion of the user using at least one second model.

The at least one processor of the electronic device may be further configured to execute the at least one instruction to: predict a first set of intermediate emotions based on the plurality of user characteristics and the combined representation of the user context, the device context and the environment context.

The at least one processor of the electronic device may be further configured to execute the at least one instruction to: provide the combined representation of the user context, the device context and the environment context to a second network and a third network; determine a local graph emotion prediction from the second network and a global node prediction from the third network; combine the local graph emotion prediction and the global node prediction based on a specific weight; and predict a second set of intermediate emotions.

According to an aspect of the disclosure, an electronic device for predicting an emotion of a user includes: at least one memory configured to store at least one instruction; at least one processor in communication with the at least one memory; and a communicator in communication with the at least one memory and the at least one processor, wherein the at least one processor is configured to execute the at least one instruction to: receive first data comprising a user activity, an operating state of the electronic device, and an operating state of at least one of one or more other electronic devices connected to the electronic device; receive second data representative of demographics and lifestyle of the user, wherein the second data is collected from at least one of the electronic device and at least one of the one or more other electronic devices connected to the electronic device; normalize the first data and the second data for input into a plurality of models; predict a plurality of user characteristics from the models; and predict the emotion of the user based on the first data, the second data, and the plurality of user characteristics.

These and other aspects of the embodiments disclosed herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein, and the embodiments herein include all such modifications.

BRIEF DESCRIPTION OF THE DRAWINGS

These and other features, aspects, and advantages of the present disclosure are illustrated in the accompanying drawings, throughout which like reference letters indicate corresponding parts in the various figures. The embodiments herein will be better understood from the following description with reference to the drawings, in which:

FIG. 2 is a flow chart illustrating a method for predicting the emotion of the user by the electronic device, according to an embodiment herein;

FIG. 3 is another flow chart illustrating the method for predicting the emotion of the user by the electronic device, according to an embodiment herein;

FIGS. 15A-15D illustrate various examples of personalization of the electronic device based on the predicted emotion of the user, according to the embodiments herein;

DETAILED DESCRIPTION

Figure 1:
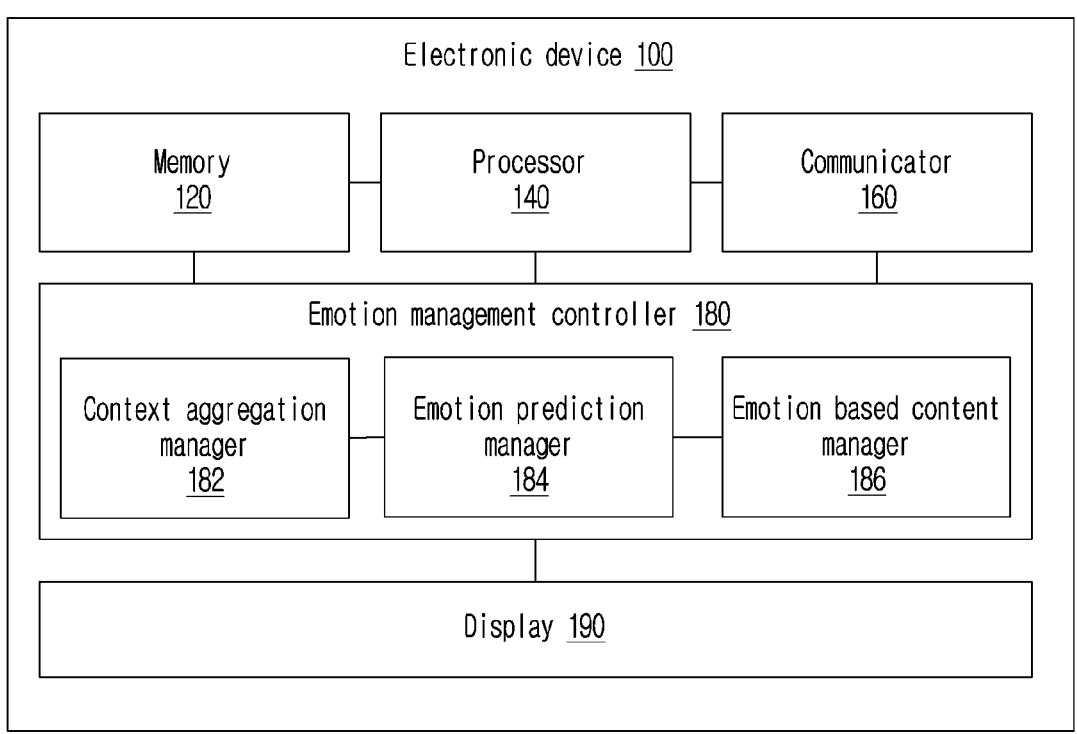
FIG. 1 is a block diagram of an electronic device for predicting an emotion of a user, according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a nonexclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits, or the like, and may optionally be driven by firmware. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms "first", "second", etc. may be used herein to describe various elements, these elements should not be limited by these terms. These terms are generally only used to distinguish one element from another.

It will be understood that when an element is referred to as being "connected" with or to another element, it can be directly or indirectly connected to the other element, wherein the indirect connection includes "connection via a wireless communication network".

Herein, the expression "at least one of a, b or c" indicates only a, only b, only c, both a and b, both a and c, both b and c, or all of a, b, and c.

Referring now to the drawings, and more particularly to FIGS. 1 through 17B where similar reference characters denote corresponding features consistently throughout the figures, FIG. 1 is a block diagram of an electronic device 100 for predicting an emotion of a user, according to an embodiment herein. Referring to FIG. 1, the electronic device 100) can be for example but not limited to a smartphone, a mobile phone, a tablet, a laptop, a palmtop, a AI speaker, an IoT sensor, a smart social robot, a Personal Digital Assistant (PDA), a music player, a video player, a wearable device, or the like.

In an embodiment, the electronic device 100) includes a memory 120, a processor 140, a communicator 160, an emotion management controller 180 and a display 190. The emotion management controller 180 is implemented by processing circuitry such as logic gates, integrated circuits, microprocessors, microcontrollers, memory circuits, passive electronic components, active electronic components, optical components, hardwired circuits, or the like, and may optionally be driven by firmware. The circuits may, for example, be embodied in one or more semiconductors.

The memory 120 is configured to store instructions to be executed by the processor 140. The memory 120 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 120 may, in some examples, be considered a non-transitory storage medium. The term "non-transitory" may indicate that the storage medium is not embodied in a carrier wave or a propagated signal. However, the term "non-transitory" should not be interpreted that the memory 120 is non-movable. In some examples, the memory 120 can be configured to store larger amounts of information. In certain examples, a non-transitory storage medium may store data that can, over time, change (e.g., in Random Access Memory (RAM) or cache).

The processor 140 communicates with the memory 120, the communicator 160 and the emotion management controller 180. The processor 140 is configured to execute instructions stored in the memory 120 and to perform various processes. The processor may include one or a plurality of processors, may be a general purpose processor, such as a central processing unit (CPU), an application processor (AP), or the like, a graphics-only processing unit such as a graphics processing unit (GPU), a visual processing unit (VPU), and/or an Artificial intelligence (AI) dedicated processor such as a neural processing unit (NPU).

The communicator 160 includes an electronic circuit specific to a standard that enables wired or wireless communication. The communicator 160 is configured to communicate internally between internal hardware components of the electronic device 100 and with external devices via one or more networks.

In an embodiment, the emotion management controller 180 includes a context aggregation manager 182, an emotion prediction manager 184 and an emotion based content manager 186.

The context aggregation manager 182 is configured to receive a user context, a device context and an environment context from the electronic device 100 and one or more other electronic devices 100 connected to the electronic device 100 and determine an aggregated version of each of the received user context, the device context and the environment context.

The emotion prediction manager 184 is configured to provide a combined representation of the user context, the device context and the environment context to a first network 184a and a plurality of intermediate models and determine a plurality of user characteristics based on the combined representation of the user context, the device context and the environment context. Determining the combined representation of the user context, the device context and the environment context includes determining a plurality of features associated with the user from the user context, the device context and the environment context and segregating the plurality of features associated with the user into a plurality of categories for a specific duration of time. Further, the emotion prediction manager 184 is configured to generate at least one vector representation for each of the plurality of categories using encoding and determine the combined representation of the user context, the device context and the environment context based on the at least one vector representation for each of the plurality of categories. The plurality of user characteristics is determined using at least one first model and wherein the emotion of the user is predicted using at least one second model.

Further, the emotion prediction manager 184 is configured to provide the combined representation of the user context, the device context and the environment context to a second network 184*b* and a third network 184*c* and determine a local graph emotion prediction from the second network 184*b* and a global node prediction from the third network 184*c*. The third network 184*c* is for example a Graph Convolution network (GCN). The emotion prediction manager 184 is configured to combine the local graph emotion prediction and the global node prediction based on a specific weight and predict a second set of intermediate emotions.

Further, the emotion prediction manager 184 is configured to provide to at least one second model, the first set of intermediate emotions and the second set of intermediate emotions along with a categorical clustering map. The emotion prediction manager 184 predicts a first set of intermediate emotions based on the plurality of user characteristics and the combined representation of the user context, the device context and the environment context. Further, the emotion prediction manager 184 is configured to perform an ensembling technique on the first set of intermediate emotions and the second set of intermediate emotions based on the categorical clustering map and predicts the emotion of the user.

Further, the emotion prediction manager 184 is configured to determine at least one of: a consumption of content by the user, abnormal usage pattern on the electronic device 100 or the one or more other electronic devices 100, a recurrence activity performed on the electronic device 100 or the one or more other electronic devices 100 by the user and a time duration spent on the electronic device 100 or the one or more other electronic device 100 by the user and determine the emotional quality of a particular feature. The quality of the predicted emotion is positive emotion or negative emotion.

In another embodiment, the emotion prediction manager 184 is configured to receive a first data comprising a user activity and an operating state of the electronic device 100 and one or more other electronic devices 100*a*-N connected to the electronic device 100 and receive a second data representative of demographics and lifestyle of the user from the electronic device 100 and one or more other electronic devices 100*a*-N connected to the electronic device 100. The emotion prediction manager 184 is configured to normalize the first data and the second data for feeding onto a plurality of models; predict a plurality of user characteristics from the models; and predict the emotion of the user from the first data, the second data and the plurality of user characteristics.

The emotion based content manager 186 is configured to perform, based on the predicted emotion of the user, modification of user experience on the electronic device 100 and the one or more other electronic devices 100*a*-N or personalization of content on the electronic device 100 and the one or more other electronic devices 100*a*-N. The emotion based content manager 186 may also be configured to perform emotional profiling on the electronic device 100 and the one or more other electronic devices 100*a*-N or generate at least one object for providing an emotional support to the user or provide a security to the user in a virtual environment or modifying at least one user parameter in the virtual environment.

The personalization of the content on the electronic device 100 includes providing animation applications like keyboard-based applications based on the predicted emotion of the user. For example, quick keyboard animation for Negative emotion (anxiety, sad) and smooth animation for positive emotion (happy, excited). Also, the personalization of content on the electronic device 100 includes providing dynamic emotion based lock. For example, when the predicted emotion of the user is anxiety, increase screen lock duration as the user tends to check smartphone frequently. Another example includes cover screen customization based on the predicted emotion of the user. The personalization of content on the electronic device 100 includes wallpaper selection based on the predicted emotion of the user. For example, providing happy images across albums on the electronic device 100.

Another example of the personalization of the content on the electronic device 100 includes automatic device color palette personalization based on the predicted emotion of the user. For example, when the emotion predicted for the user is angry then the device color palette may be turned red, yellow may be used for happy, black for fear, etc.

In another example, the personalization of the content on the electronic device 100 is provided by prioritizing between emotional interactions and performance based interaction based on the predicted emotion of the user and his/her response to personalization. For example, when the user is happy and excited, then emotional appeal is greater than performance. Therefore, the electronic device 100 provides varied animations, vibrant color palette themes, etc.

When the user is in a hurry or stressed, then the performance requirement is greater than the emotional appeal. Therefore, no animation is provided by the electronic device 100, single themes like dark mode, etc. are displayed so that the performance is higher.

The emotion based content manager 186 provides insight level experiences. For example, the emotion based content manager 186 provides insights to the user such as for example, with whom the user has been happy based on conversation or call, etc., which application usage has made the user very happy (or sad), then based on the insight level experience the user may choose to install or uninstall applications, accordingly.

At least one of the plurality of modules/components of the emotion management controller 180 may be implemented through an AI model. A function associated with the AI model may be performed through memory 120 and the processor 140. The one or a plurality of processors controls the processing of the input data in accordance with a predefined operating rule or the AI model stored in the non-volatile memory and the volatile memory. The predefined operating rule or artificial intelligence model is provided through training or learning.

Here, being provided through learning means that, by applying a learning process to a plurality of learning data, a predefined operating rule or AI model of a desired characteristic is made. The learning may be performed in a device itself in which AI according to an embodiment is performed, and/or may be implemented through a separate server/system.

The AI model may consist of a plurality of neural network layers. Each layer has a plurality of weight values and performs a layer operation through calculation of a previous layer and an operation of a plurality of weights. Examples of neural networks include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks.

The learning process is a method for training a predetermined target device (for example, a robot) using a plurality of learning data to cause, allow, or control the target device to make a determination or prediction. Examples of learning processes include, but are not limited to, supervised learning, unsupervised learning, semi-supervised learning, or reinforcement learning.

In an embodiment, the display 190 is configured to display personalized content based on the predicted emotion of the user of the electronic device 100. The display 190 is capable of receiving inputs and is made of one of liquid crystal display (LCD), light emitting diode (LED), organic light-emitting diode (OLED), etc.

Although FIG. 1 shows various hardware components of the electronic device 100, it is to be understood that other embodiments are not limited thereto. In other embodiments, the electronic device 100 may include a larger or smaller number of components. Further, the labels or names of the components are used only for illustrative purpose and does not limit the scope of the disclosure. One or more components can be combined together to perform same or substantially similar function to predicting the emotion of the user by the electronic device 100.

FIG. 2 is a flow chart illustrating a method 200 for predicting the emotion of the user by the electronic device 100, according to an embodiment herein.

Referring to FIG. 2, at operation 202, the method 200 includes the electronic device 100 receiving the user context, the device context and the environment context from the electronic device 100 and one or more other electronic devices 100*a*-N connected to the electronic device 100. For example, in the electronic device 100 described in FIG. 1, the emotion management controller 180 is configured to receive the user context, the device context and the environment context from the electronic device 100 and one or more other electronic devices 100*a*-N connected to the electronic device 100.

At operation 204, the method 200 includes the electronic device 100 determining the combined representation of the user context, the device context and the environment context. For example, in the electronic device 100 described in FIG. 1, the emotion management controller 180 is configured to determine the combined representation of the user context, the device context and the environment context.

At operation 206, the method 200 includes the electronic device 100 determining the plurality of user characteristics based on the combined representation of the user context, the device context and the environment context. For example, in the electronic device 100 described in FIG. 1, the emotion management controller 180 is configured to determine the plurality of user characteristics based on the combined representation of the user context, the device context and the environment context.

At operation 208, the method includes the electronic device 100 predicting the emotion of the user based on the combined representation of the user context, the device context, the environment context and the plurality of user characteristics. For example, in the electronic device 100 described in FIG. 1, the emotion management controller 180 is configured to predict the emotion of the user based on the combined representation of the user context, the device context, the environment context and the plurality of user characteristics.

The various actions, acts, blocks, operations, or the like in the flow chart of FIG. 2 may be performed in the order presented, in a different order or simultaneously. Further, in some embodiments, some of the actions, acts, blocks, operations, or the like may be omitted, added, modified, skipped, or the like without departing from the scope of the disclosure.

FIG. 3 is another flow chart illustrating the method 300 for predicting the emotion of the user by the electronic device 100, according to an embodiment herein.

Referring to FIG. 3, at operation 302, the method includes the electronic device 100 receiving the first data including the user activity and the operating state of the electronic device 100 and one or more other electronic devices 100*a*-N connected to the electronic device 100. The user activity can be for example, user response in a specific application, user ordering a specific variety of food at a specific time, user going to a gym, user routine, etc. The operating state of the electronic device 100 can be for example but not limited to connecting capability to Wi-Fi or Bluetooth, battery capability, memory available, video calls available or not, etc. For example, in the electronic device 100 described in FIG. 1, the emotion management controller 180 is configured to receive the first data including the user activity and the operating state of the electronic device 100 and one or more other electronic devices 100*a*-N connected to the electronic device 100.

At operation 304, the method includes the electronic device 100 receiving the second data representative of demographics and lifestyle of the user from the electronic device 100 and one or more other electronic devices 100*a*-N connected to the electronic device 100. For example, in the electronic device 100 described in FIG. 1, the emotion management controller 180 is configured to receive the second data representative of demographics and lifestyle of the user from the electronic device 100 and one or more other electronic devices 100*a*-N connected to the electronic device 100.

At operation 306, the method 300 includes the electronic device 100 normalizing the first data and the second data for feeding onto the plurality of models. For example, in the electronic device 100 described in FIG. 1, the emotion management controller 180 is configured to normalize the first data and the second data for feeding onto the plurality of models.

At operation 308, the method 300 includes the electronic device 100 predicting the plurality of user characteristics from the models. For example, in the electronic device 100 described in FIG. 1, the emotion management controller 180 is configured to predict the plurality of user characteristics from the models.

At operation 310, the method 300 includes the electronic device 100 predicting the emotion of the user from the first data, the second data and the plurality of user characteristics. For example, in the electronic device 100 described in FIG. 1, the emotion management controller 180 is configured to predict the emotion of the user from the first data, the second data and the plurality of user characteristics.

The various actions, acts, blocks, operations, or the like in the flow chart of FIG. 3 may be performed in the order presented, in a different order or simultaneously. Further, in some embodiments, some of the actions, acts, blocks, operations, or the like may be omitted, added, modified, skipped, or the like without departing from the scope of the disclosure.

Figure 4:
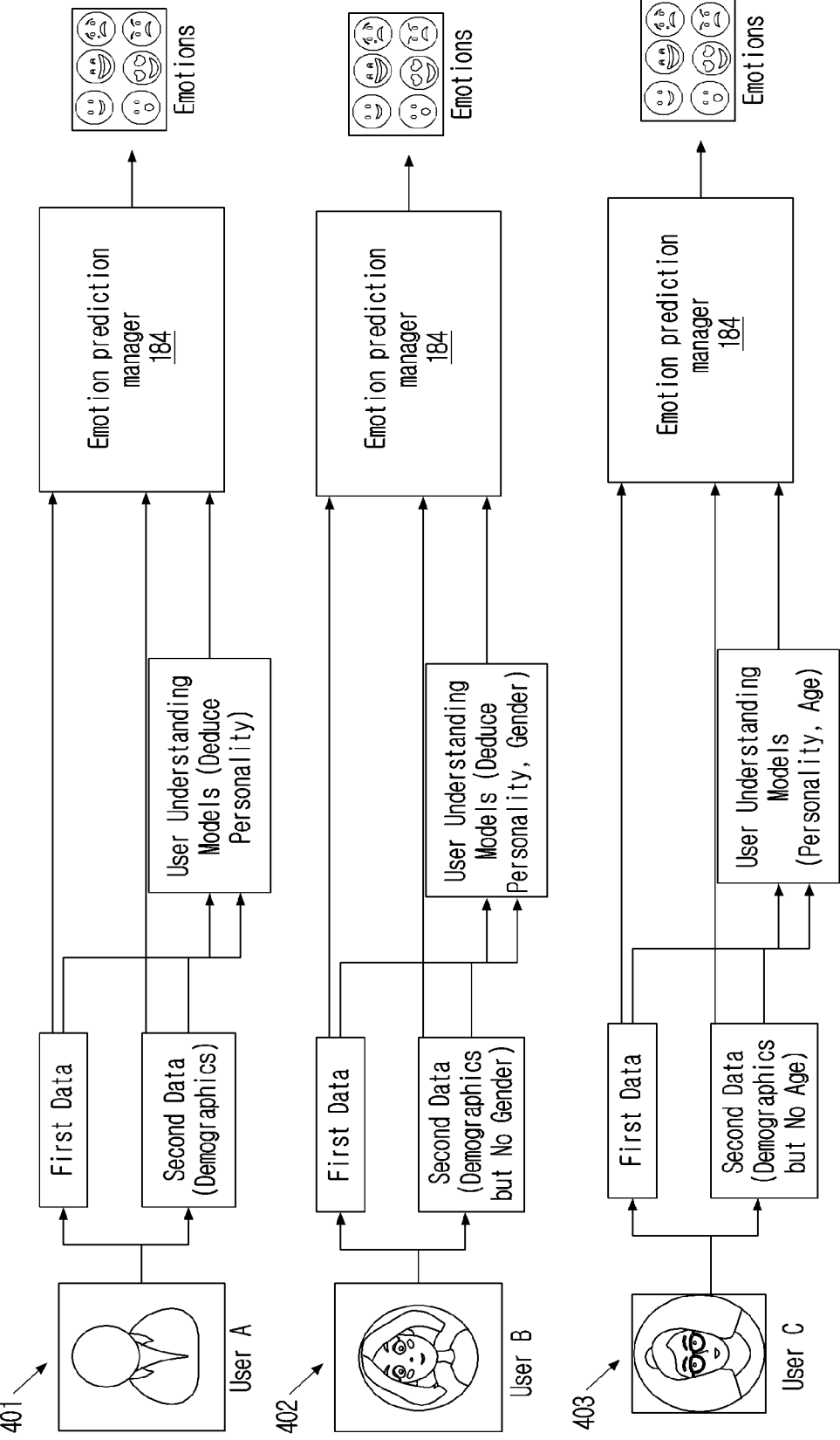
FIG. 4 is an example illustrating an inference flow for predicting the emotion of the user by the electronic device, according to the embodiments herein.

FIG. 4 is an example illustrating an inference flow for predicting the emotion of the user by the electronic device 100, according to the embodiments described herein.

Referring to FIG. 4, consider various users and various data availability. At operation 401, consider the case of user A where the first data (e.g., data associated with the electronic device 100) is available along with second data which is demographic data. The first model is used to deduce personality of the user. Then user personality data, along with the first data and the second data, is provided to the emotion prediction manager 184 to predict the emotions of the user A.

Similarly, at operation 402, consider the case of user B where the first data (e.g., data associated with the electronic device 100) is available along with second data which is demographic data without gender details of the user B. The first model is used to deduce personality of the user along with the gender details of the user B. Then the user personality data, and the gender details of the user B along with the first data and the second data are provided to the emotion prediction manager 184 to predict the emotions of the user B.

Similarly, at operation 403, consider the case of user C where the first data (e.g., data associated with the electronic device 100) is available along with second data which is demographic data without age details of the user C. The first model is used to deduce personality of the user along with the age details of the user C. Then the user personality data, and the age details of the user C along with the first data and the second data are provided to the emotion prediction manager 184 to predict the emotions of the user C.

Figure 5A:
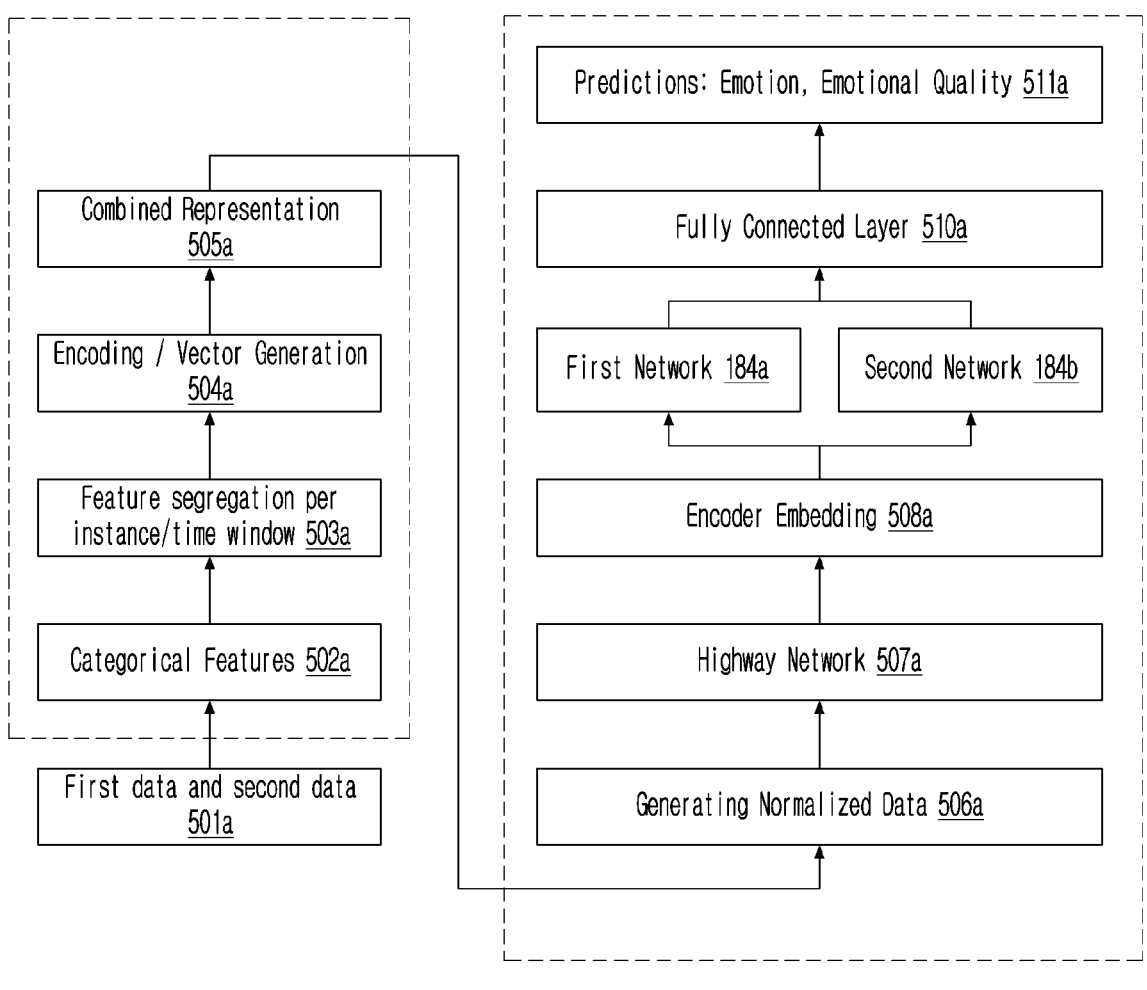
FIGS. 5A-5B illustrate various actions involved in the prediction of the emotion by the electronic device, according to the embodiments herein.
Figure 5B:
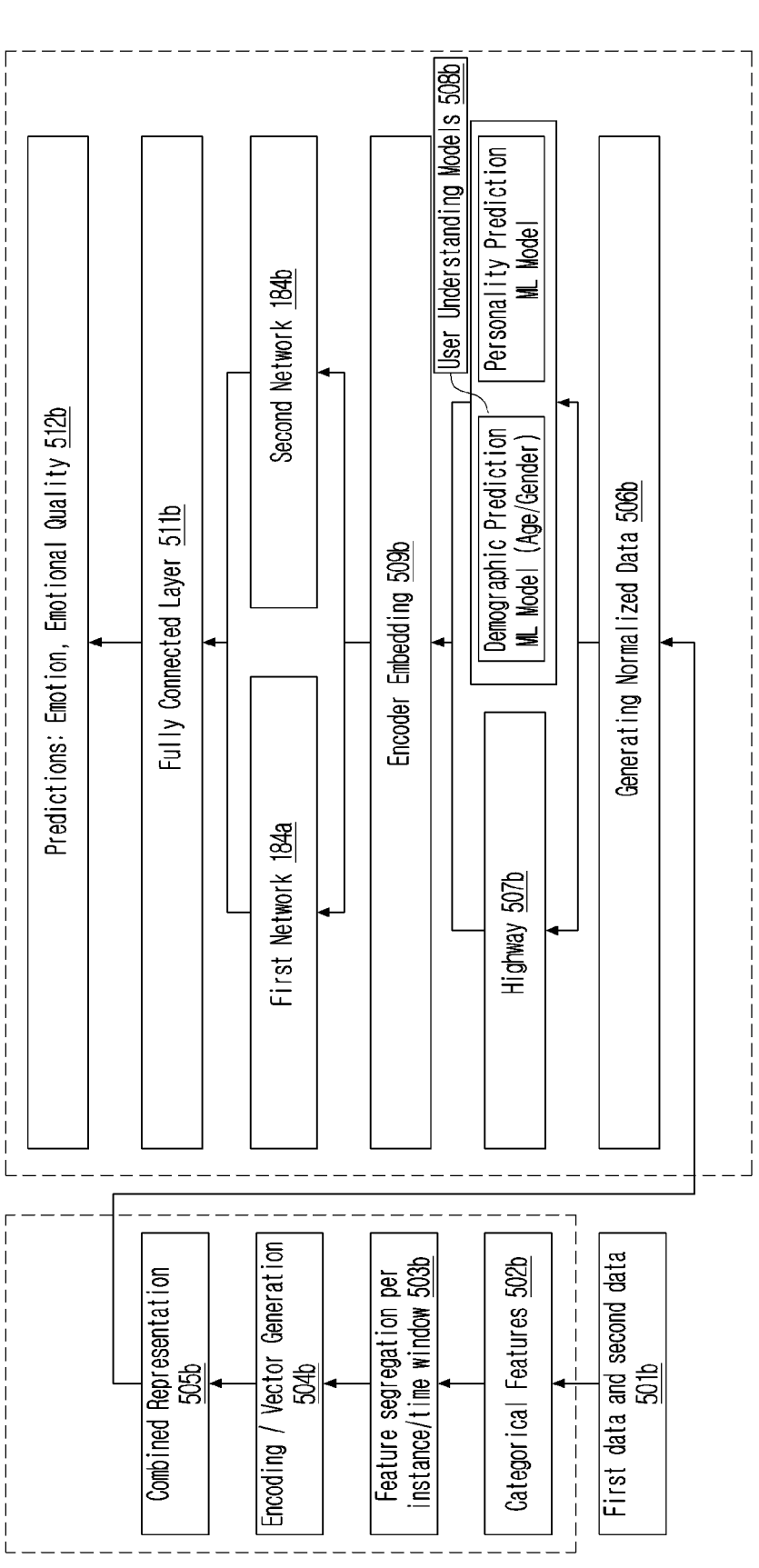

FIGS. 5A-5B illustrate various actions involved in the prediction of the emotion by the electronic device 100, according to the embodiments described herein.

Referring to FIG. 5A, at operation 501a, the first data and the second data are provided to the electronic device 100. At operation 502a, the categorical features are determined and at operation 503a, the categorical features are segregated per instance/time window. At operation 504a, the encoding and vector generation is performed. At operation 505a, the combined representation is generated, and at operation 506a normalized data is generated. At operation 507a, the normalized data is passed through a highway network, and at operation 508a the encoder embedding is performed. Further, the encoded data are sent through a first network 184a which can be, for example, and auto encoder network 184a and a second network 184b which can be, for example, a Graph Isomorphism Network 184b. At operation 510a, the output from both the first network 184a and the second network are sent through the fully connected layer, and at operation 511a the emotion of the user is predicted along with the emotional quality.

Referring to FIG. 5B, in conjunction with FIG. 5A, operations 501a-507a are the same as 501b-507b. However, FIG. 5B includes demographic prediction ML model (Age/Gender) and personality prediction ML Model. Here, the demographic prediction ML model and the personality prediction ML Model can be used independently to determine demographic data or personality related data. This pipeline is used when the first data and the second data are missing certain user information such as a user's gender, a user's age, etc.

Figure 6A:
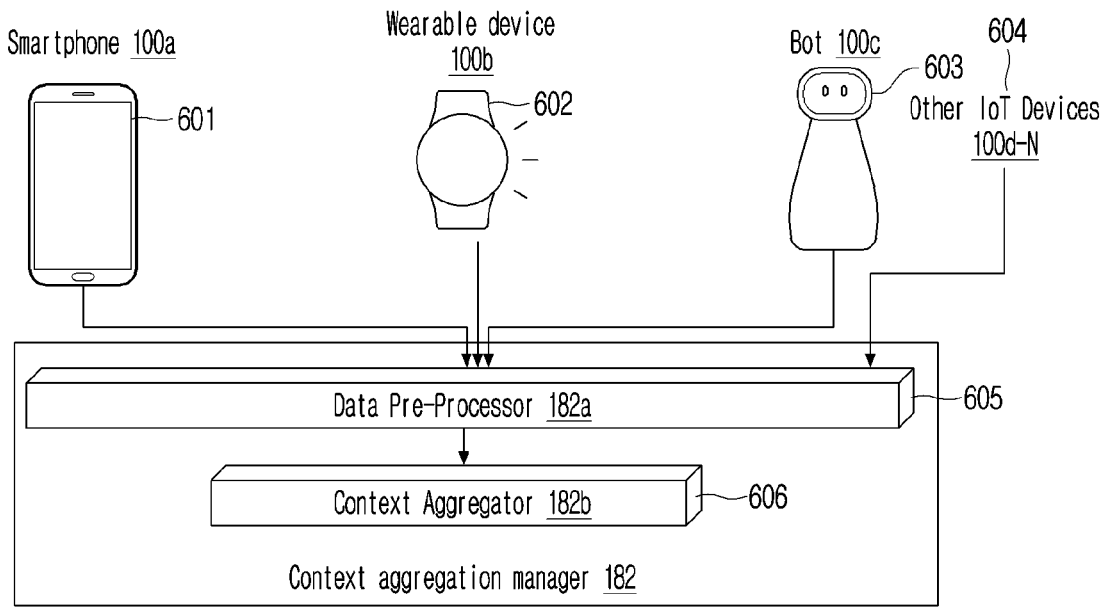
FIGS. 6A-6C are examples illustrating the aggregation of the device context, the environmental context and the user context by a context aggregation manager, according to the embodiments herein.
Figure 6B:
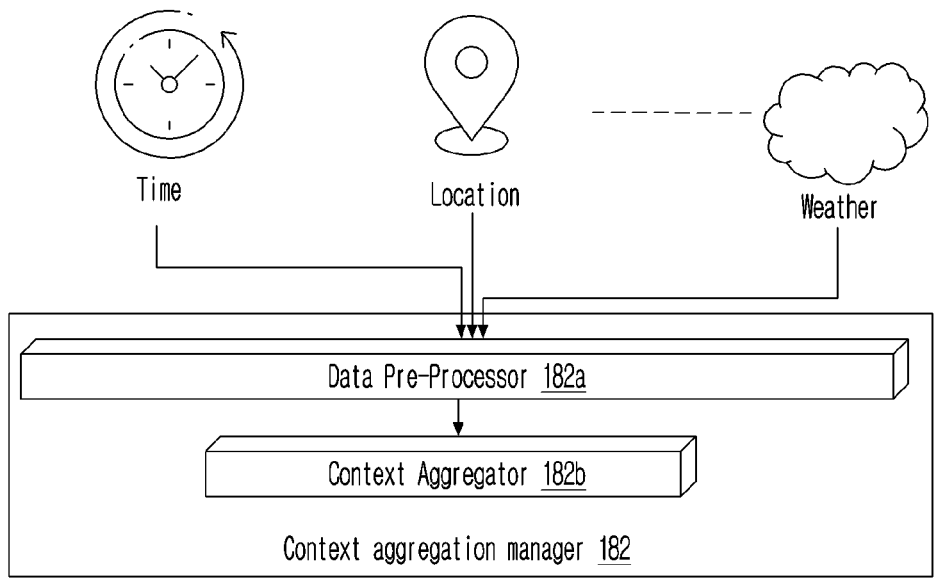
Figure 6C:
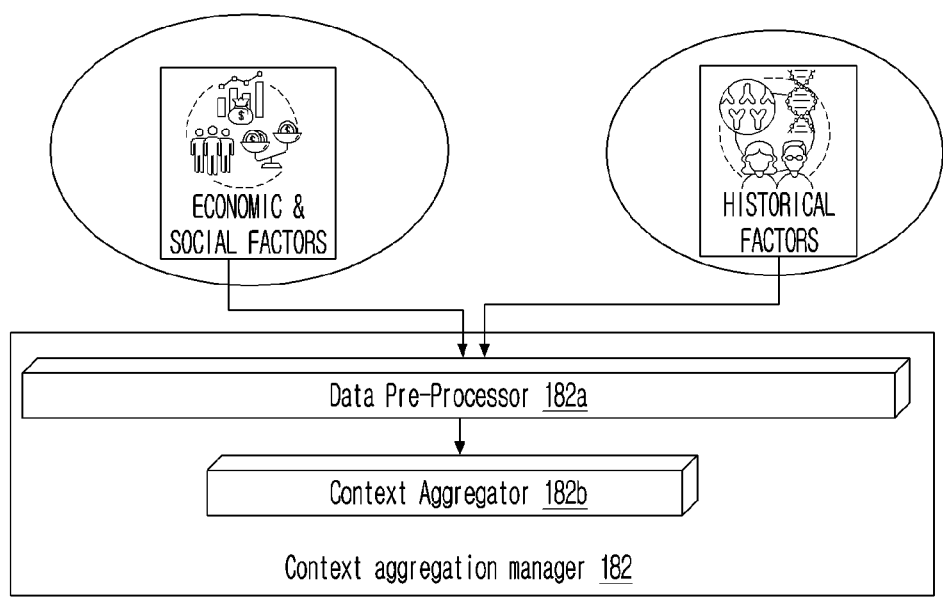

FIGS. 6A-6C are examples illustrating the aggregation of the device context, the environmental context and the user context by the context aggregation manager 182, according to the embodiments described herein.

Referring to FIG. 6A, consider various electronic devices 100a-N of the user such as smartphone 100a, a wearable device 100b, Bot 100c and other IoT devices 100d-N. At operation 601, the context aggregation manager 182 receives the device context from the smartphone 100a. Here, the device context is determined based on, for example but not limited to, usage of Wi-Fi, GPS, microphone, etc. At operation 602, the context aggregation manager 182 receives the device context from the wearable device 100b which includes heart rate, blood pressure, sleep pattern, etc. associated with the user. At operation 603, the context aggregation manager 182 receives the device context from the bot 100c which includes details such as available videos, images, audio files, etc. Similarly, at operation 604, the context aggregation manager 182 receives the device context from the other IoT devices 100d of the user. At operation 605, a data pre-processor 182a performs data filtering and arrangement. At operation 606, a context aggregator 182b aggregates similar data received from different devices of the user.

Similarly, in FIG. 6B, the environment context is received and aggregated which includes various environmental factors such as for example but not limited to location, time, weather conditions, temperature, humidity, etc.

Similarly, in FIG. 6C, the user context is received and aggregated which includes economic and social factors such as culture, finance, assets, etc. and historical factors of the user such as for example personality, situational emotion, family, decisions, etc.

Figure 7:
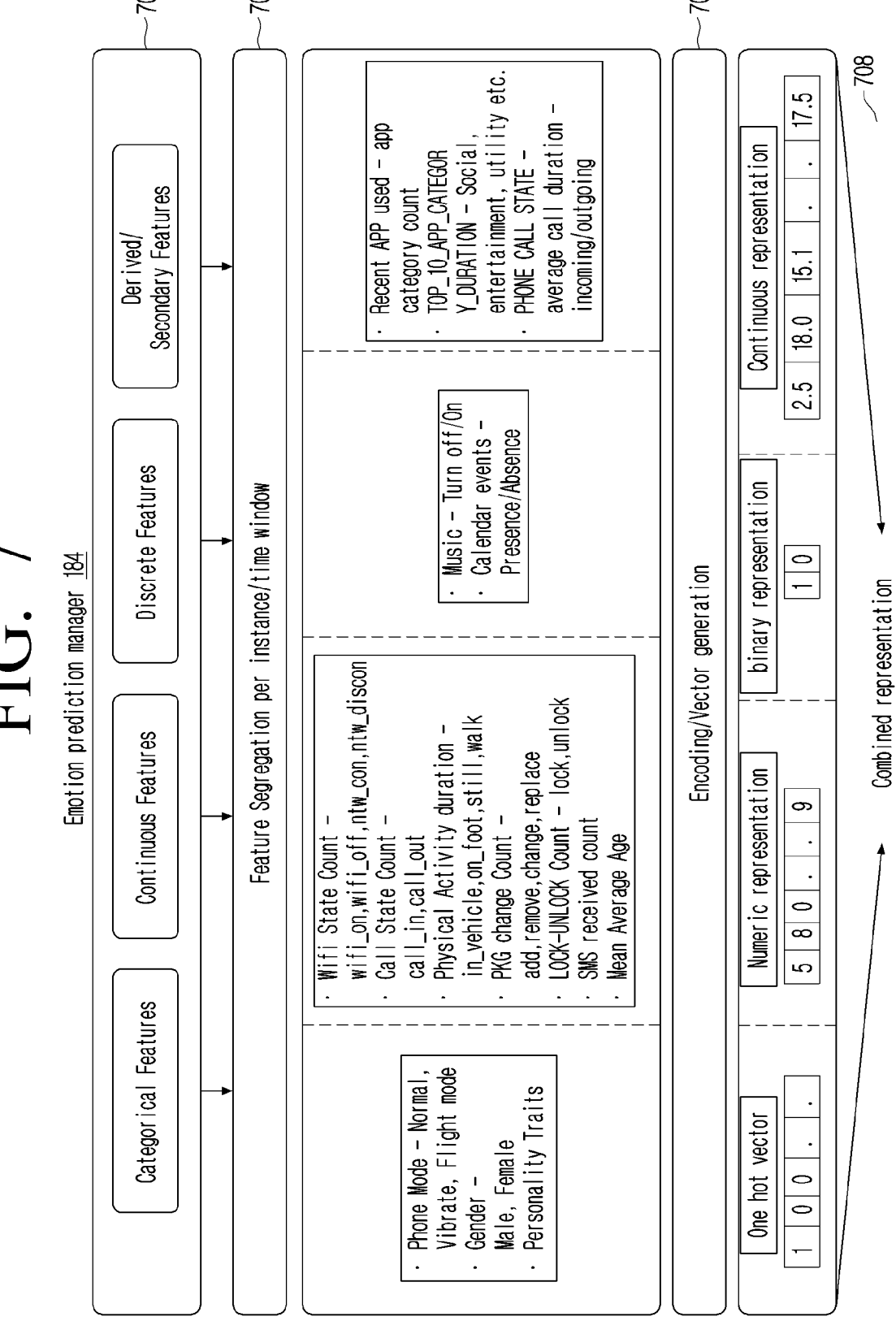
FIG. 7 is a block diagram illustrating categorical data interpretation and representation by an emotion prediction manager, according to the embodiments herein.

FIG. 7 is a block diagram illustrating categorical data interpretation and representation by the emotion prediction manager 184, according to the embodiments described herein. Referring to FIG. 7, at operation 702, the first data and the second data are separated into categorical features, continuous features, discrete features and derivative (or secondary) features. At operation 704, feature segregation per instance/time window is performed. At operation 706, encoding and vector generation is performed on the segregated data. The encoding and vector generation schemes can be, for example, one hot vector, numeric representation, binary representation and continuous representation. Further, at operation 708, the combined representation of the encoded data is obtained.

Figure 8:
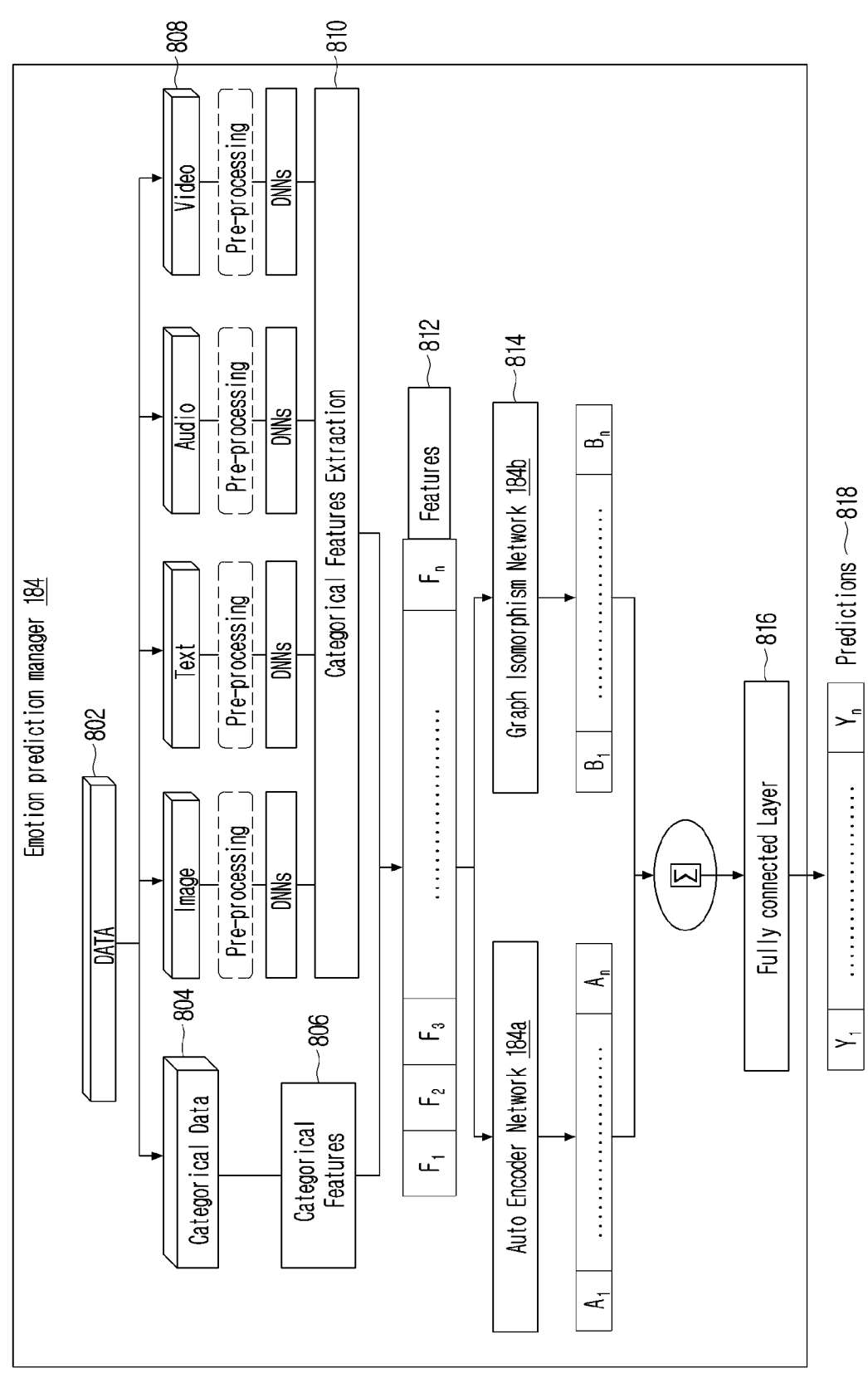
FIG. 8 is a block diagram illustrating categorical fusion network (CaFuNet) of the emotion prediction manager, according to the embodiments herein.

FIG. 8 is a block diagram illustrating a categorical fusion network (CaFuNet) of the emotion prediction manager 184, according to the embodiments described herein. Referring to FIG. 8, at operation 802, the data is available, at operation 804 the categorical data is obtained, and at operation 806 the categorical features are obtained. Also, at operation 808, the data is divided into image, text, audio and video. The data is pre-processed and passed through corresponding DNN models to get the categorical features (operation 810). The categorical features obtained both at operation 806 and operation 810 are combined at operation 812 to obtain the features. At operation 814, the combined data is passed through the auto encoder network (i.e., first network) 184a and the graph isomorphism network (i.e., second network) 184b. The outputs from both networks are combined using an adder and passed through the fully connected layer (operation 816) to predict the emotions of the user (operation 818).

Figure 9:
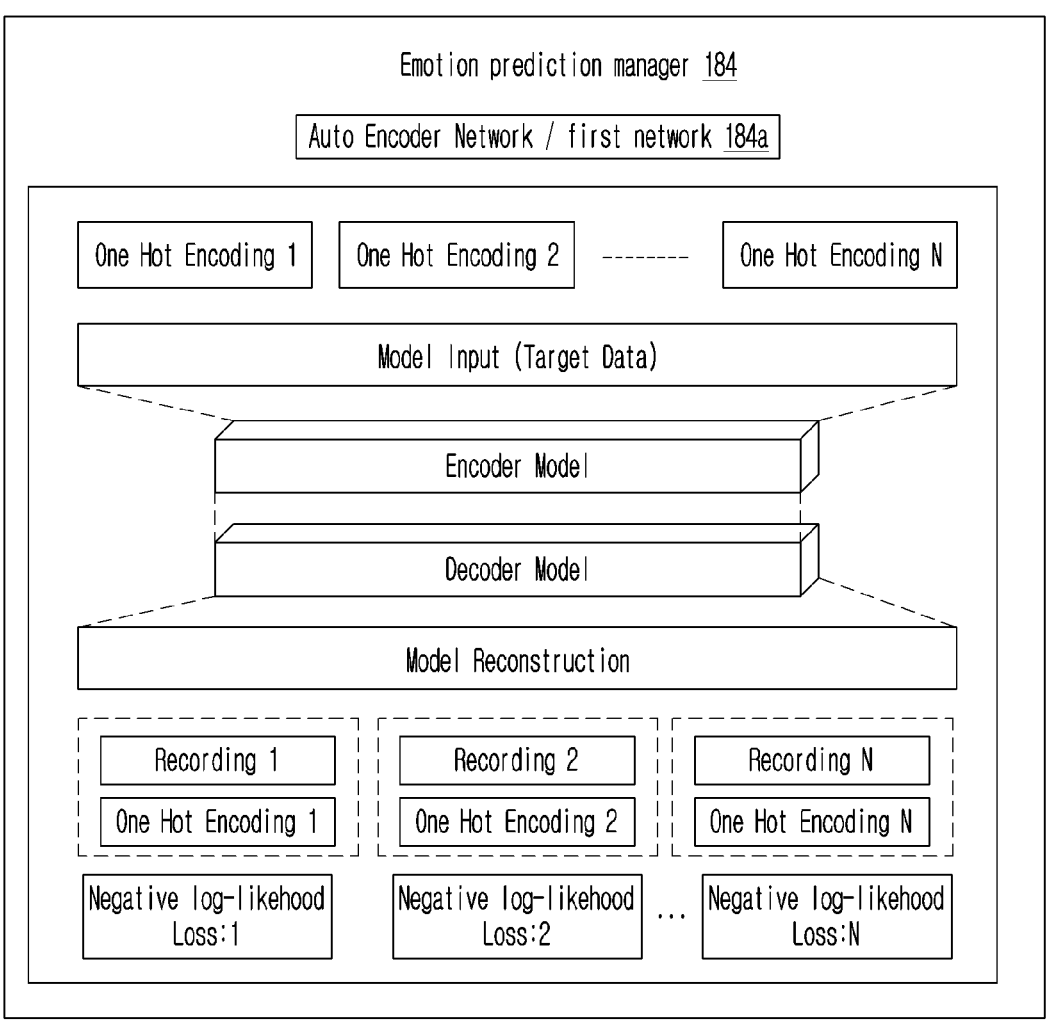
FIG. 9 is a block diagram illustrating CaFuNet with user Understanding Models of the emotion prediction manager, according to the embodiments herein.

FIG. 9 is a block diagram illustrating CaFuNet with user Understanding Models of the emotion prediction manager 184, according to the embodiments herein.

Referring to FIG. 9, various user understanding models with the various layers of the auto-encoder network 184a are provided.

Figure 10:
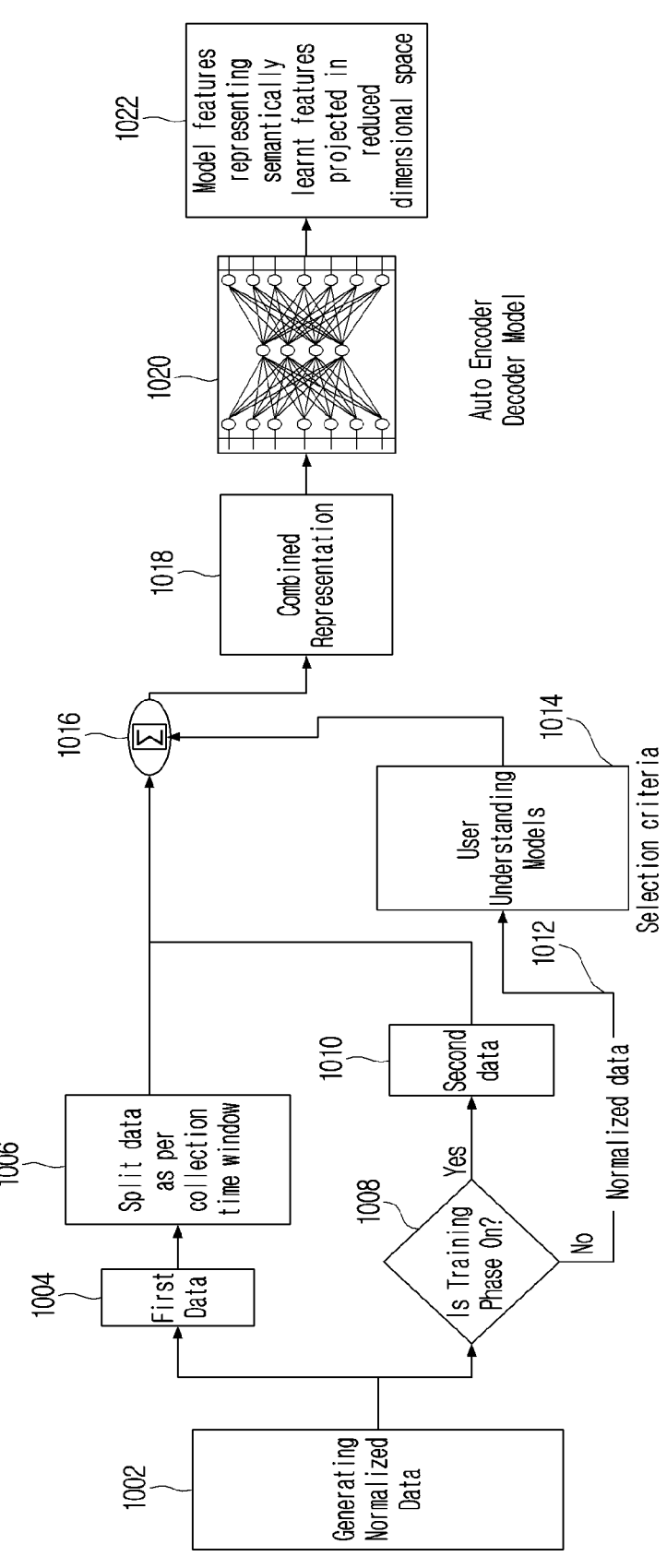
FIG. 10 is flow chart illustrating functioning of a deep neural network (DNN) to capture sematic information like an auto encoder network, according to the embodiments herein.

FIG. 10 is flow chart illustrating functioning of a DNN to capture sematic information like the auto encoder network 184a, according to the embodiments described herein. Referring to FIG. 10, at operation 1002, normalized data is generated and at operation 1004, the first data is received by the electronic device 100. At operation 1006, the first data is split as per collection time window. At operation 1008, the electronic device 100 determines if the training phase is on, and if not, the normalized data is sent to the user understanding models 1012 and 1014. If the training phase is ON, then at operation 1010, the second data is received by the electronic device 100. Further, at operation 1016, an adder receives the data from operations 1006, 1010 and 1014, and at operation 1018 the combined representation is provided. The combined representation is then sent to the auto encoder network 184*a* (operation 1020). At operation 1022, the model features representing semantically learned features are projected in reduced dimensional space.

Figure 11:
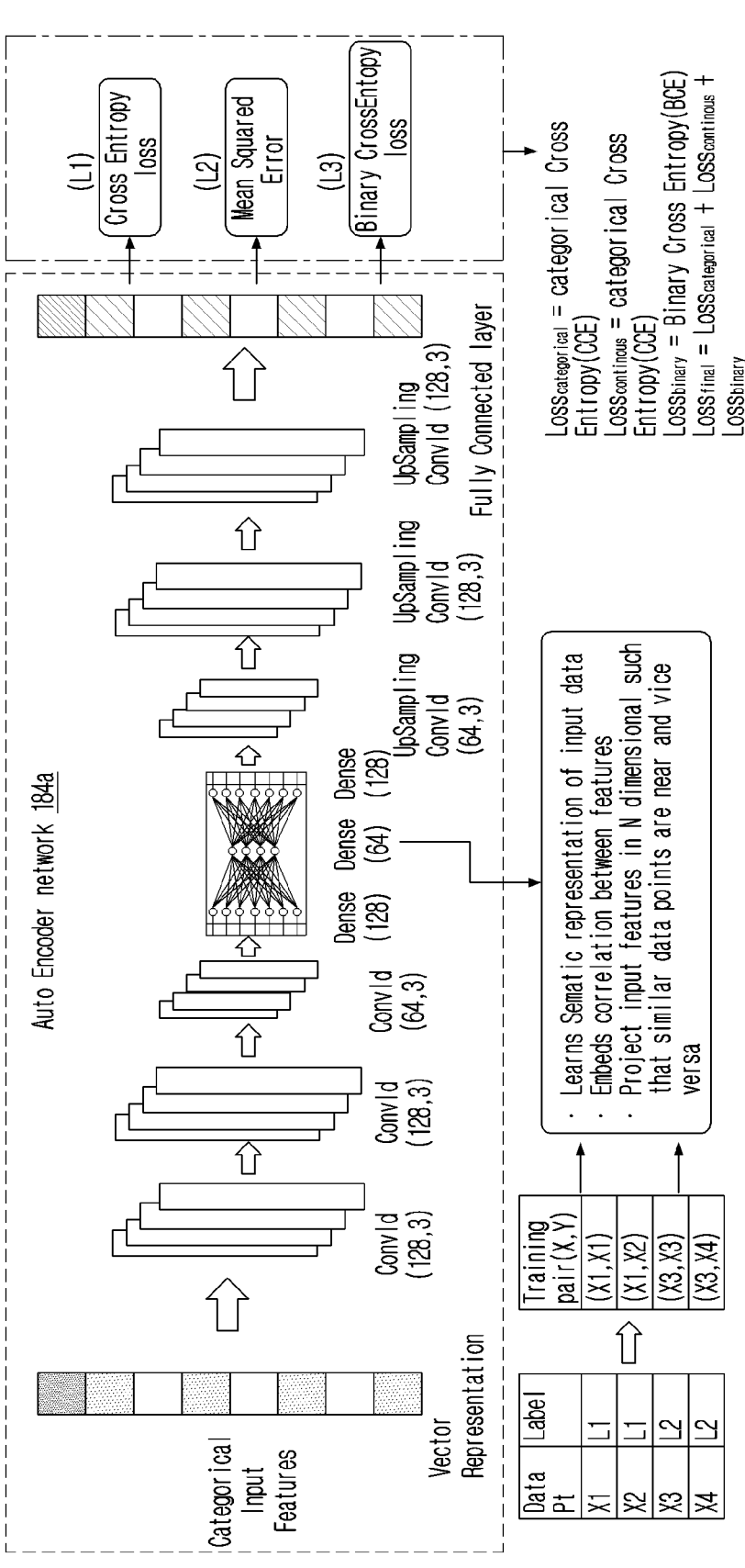
FIG. 11 is a block diagram illustrating auto encoder network, according to the embodiments herein.

FIG. 11 is a block diagram illustrating the auto encoder network 184*a*, according to the embodiments described herein. Model features representing semantically learned features are projected in reduced dimensional space. The auto encoder network 184*a*, enables dimensionality reduction for large number features of data. The auto encoder network 184*a*, inherently reduces training and inference time of follow up model as number of features are reduced and enables follow up layers to converge more quickly. The auto encoder network 184*a* learns sematic representation of input data and thus assists following layers in better modelling of patterns.

The auto encoder network 184*a* embeds correlation between inter related features and project input features in N dimensional such that similar data points are near and vice versa.

For purposes of this disclosure, the term "Input Data" means First Data: comprising user activity non-private data on a user device (per collection time window); the term "Second Data" means data comprising demographics and lifestyle of the user from the user device. For purposes of this disclosure, the term "Training Phase" refers to collection of raw user data (Age, Gender, Personality etc.), and the term "Inference Phase" means output of User Understanding models of missing second data and second data.

Figure 12:
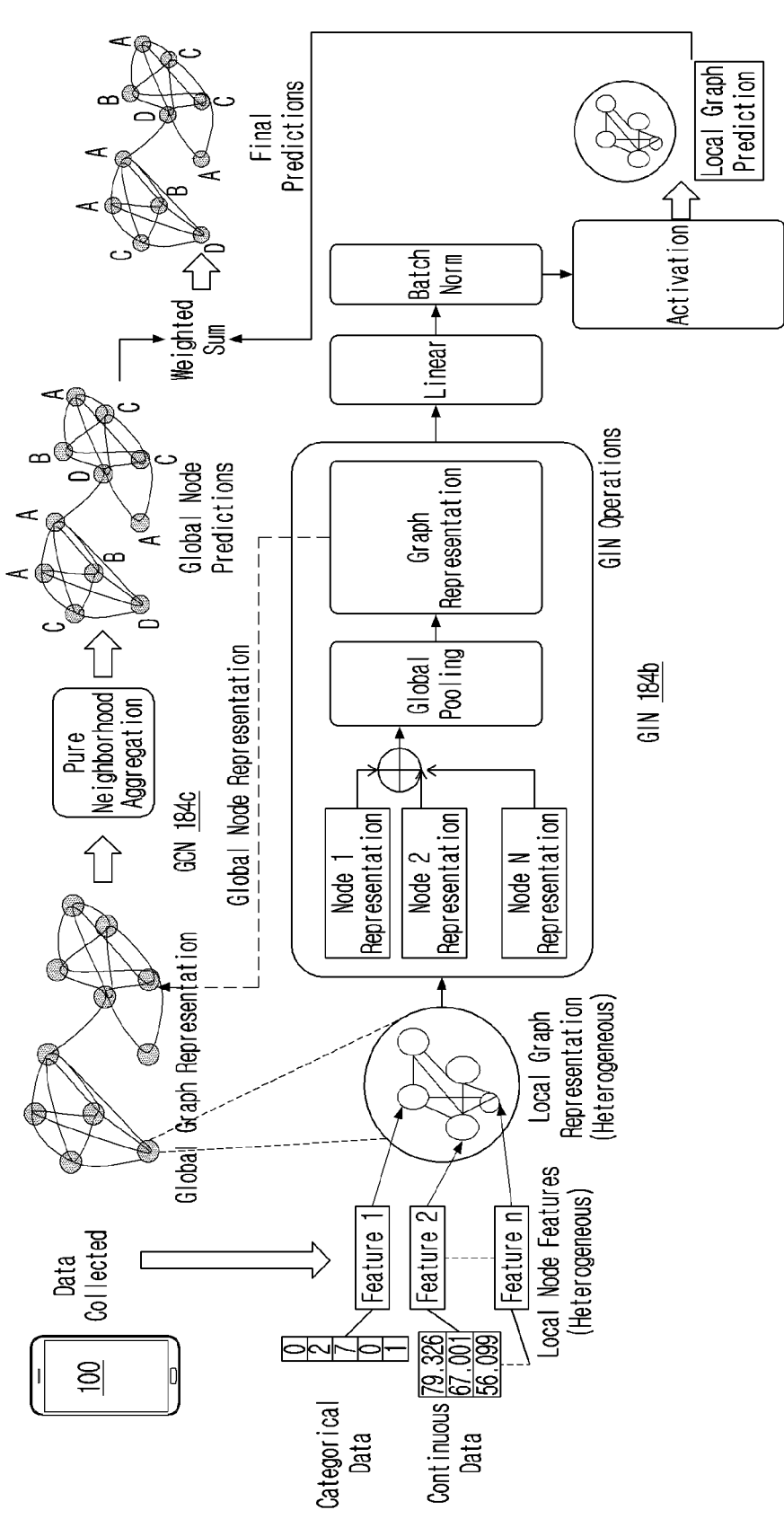
FIG. 12 is a block diagram illustrating functioning of a DNN to capture structural and sequential information like Graph Isomorphism network (GIN) with Graph Convolution network (GCN), according to the embodiments herein.

FIG. 12 is a block diagram illustrating functioning of a DNN to capture structural and sequential information like the Graph Isomorphism network (GIN) 184*b* with the Graph Convolution network (GCN) 184*c*, according to the embodiments described herein. Referring to FIG. 12, model features representing structural and sequential information of data are provided. The GIN 184*b* is used because the data can be better structured and explained as a graph. There is inherent co-relation in the first data (user activity and operating state data) obtained from within and across users and thus can be represented as nodes of the graph.

Sequential information (time information) and the second data (representative of demographics and lifestyle of the user from the user device and/or devices connected to the user device) can be structurally better represented through connections of the graph. The GNNs can process any kind of graph. The GIN 184*b* maximizes the representations of nodes (through better aggregations). Here, the nodes is first data from user(s) (per collection time window) and edges are of two types: within-user and inter-user. "Within-user" refers to previous 'N' and next 'M' consecutive windows (in total 'N'+'M' within-user edges), for example, temporal features, timing info. "Inter-user" refers to choose 1' most closest (through similarity measurement), for example, similarity of personality.

Figure 13:
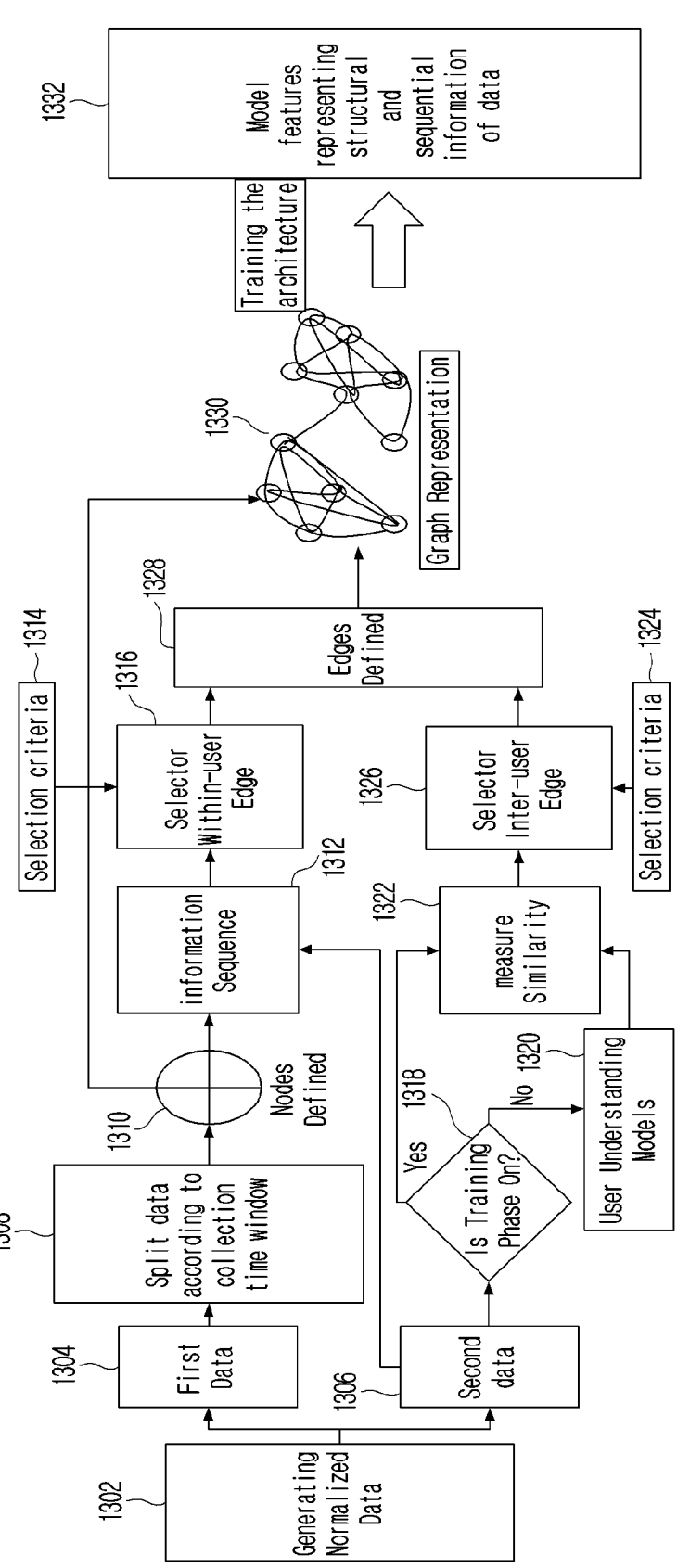
FIG. 13 is a flow chart illustrating the graph operations, according to the embodiments herein.

FIG. 13 is a flow chart illustrating the graph operations, according to the embodiments herein. Referring to FIG. 13, at operation 1302 the normalized data is generated. At operations 1304 and 1306, the electronic device 100 receives the first data and the second data respectively. At operation 1308, the electronic device 100 determines the split data according to collection time window. At operation 1310, the adder is provided with the split data and the second data; and at operation 1312, the sequence information is obtained. At operation 1316, within-user Edge Selector obtains the selection criteria from operation 1314.

At operation 1318, the electronic device 100 determines whether the training phase is on. In response to determining that the training phase is not On, the user understanding models are provided with the second data (operation 1320). At operation 1322, the similarity measure is determined. At operation 1326, inter-user edge selector obtains selection criteria from operation 1324. At operation 1328, the graph edges are defined and at operation 1330, the graph representation is obtained. At operation 1332, the model features representing structural and sequential information of data is obtained.

Figure 14:
FIG. 14 illustrates an example of insight level experiences being provided based on the predicted emotion of the user, according to the embodiments herein.

FIG. 14 illustrates an example of insight level experiences being provided based on the predicted emotion of the user, according to the embodiments herein.

Referring to FIG. 14, at operation 1401, the electronic device 100 provides emotional profiling to the user based on the predicted emotions over a period of time. For example, emotional Stats and well-being, enhance emotional health overtime, emotional habit formation (daily, weekly, monthly, etc.).

At operation 1402, the electronic device 100 provides insights to user like with contact of the user, was the user happy based on conversation or call, etc., which application the user has been very happy and/or sad with. This can be used to decide on the type of applications which can be installed or uninstalled accordingly.

FIG. 15A-15D illustrates various examples of personalization of the electronic device 100 based on the predicted emotion of the user, according to the embodiments described herein.

Referring to FIG. 15A, illustrates prioritization of favorite contacts. Referring to operation 1501*a*, consider an example where the predicted emotion of the user is "Surprise". And, when the user is surprised, the user tends to talk to close friends. Consequently, the contact list is modified accordingly. Referring to operation 1502*a*, consider an example where the predicted emotion of the user is "Fear". And, when the user is fearful, the user tends to talk to family; therefore, the contact list is modified to display the contacts of family members on top.

Referring to FIG. 15B, illustrates search result prioritization. At operation 1501*b*, consider an example where the predicted emotion of the user is "Happy". And, when the user is happy, the user tends to share social media status. Therefore, the social networking site applications are prioritized over other applications and presented to the user. At operation 1502*b*, consider an example where the predicted emotion of the user is "Sad". And, the user tends to discuss with friends when sad, therefore, the chat applications are prioritized and provided to the user.

Similarly, referring to FIG. 15C, at operation 1501*c*, the conventional calendar application is provided. At operation 1502*c*, the calendar sticker personalization is performed based on the predicted emotion of the user.

Referring to FIG. 15D, at operation 1501*d*, the conventional reply option is provided when the user tries to reply form a notification panel. At operation 1502*d*, the emotion based ideographic smart reply suggestions are provided in the proposed method. Additionally, adaptive notification UI (color and styling) based on emotion of the text to prioritize among cluttered notifications may be employed. Similarly, it can be used for adaptive color palette and dialogue box tone, etc.

FIGS. 16A-16D illustrates examples of using the predicted emotion for creating digital twin in the Metaverse, according to the embodiments herein.

Figure 16A:
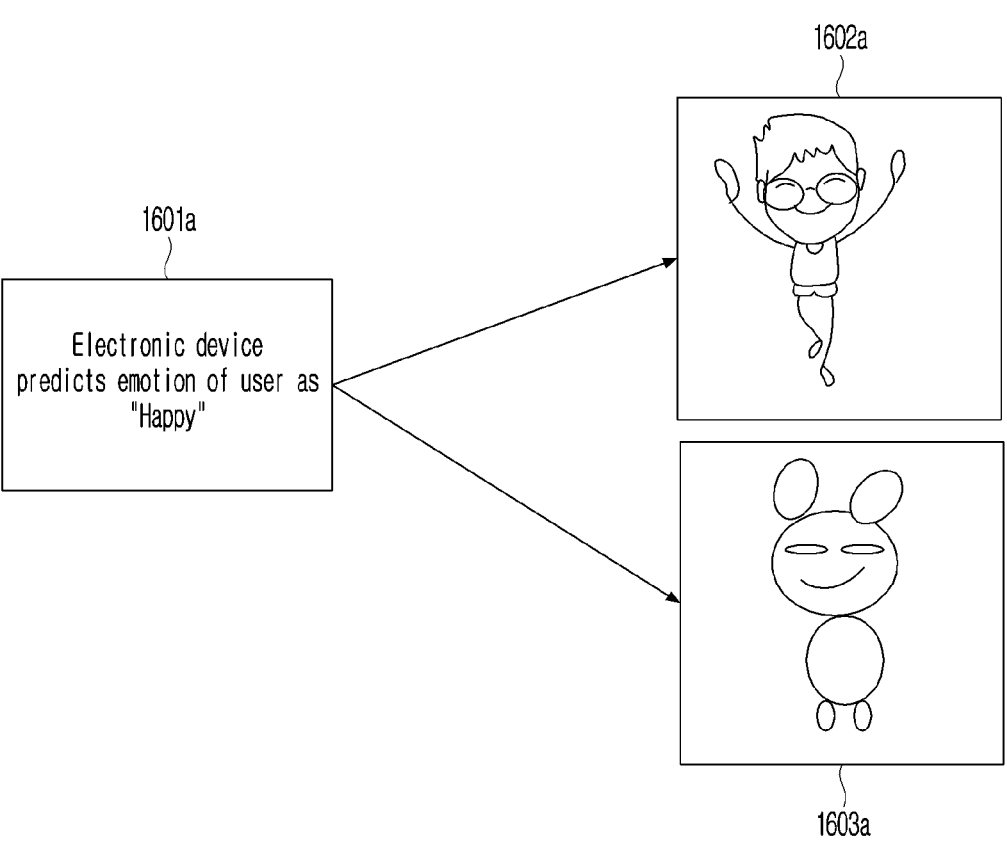
FIGS. 16A-16D illustrate examples of using the predicted emotion for creating digital twin in a virtual environment, according to the embodiments herein.

Referring to FIG. 16A, at operation 1601*a* consider that the electronic device 100 predicts that the emotion of the user is "Happy". Then at operation 1602*a*, the electronic device 100 replicates the predicted emotion of the user (i.e., "Happy") in a virtual setting. At operation 1603*a*, the electronic device 100 defines a custom behavior of the user as per the predicted emotion in the virtual setting. Therefore, in the proposed method the predicted emotion of the user is reflected in the virtual setting both in behavior and avatars.

Figure 16B:

Similarly, in FIG. 16B, the digital twin (i.e., the avatar) of the user in the virtual setting changes based on the predicted emotions of the user. FIG. 16B provides various examples for avatars replicating the emotions predicted by the electronic device 100 such as for example, anxiety, sad, happy, disgust, angry, etc.

Figure 16C:
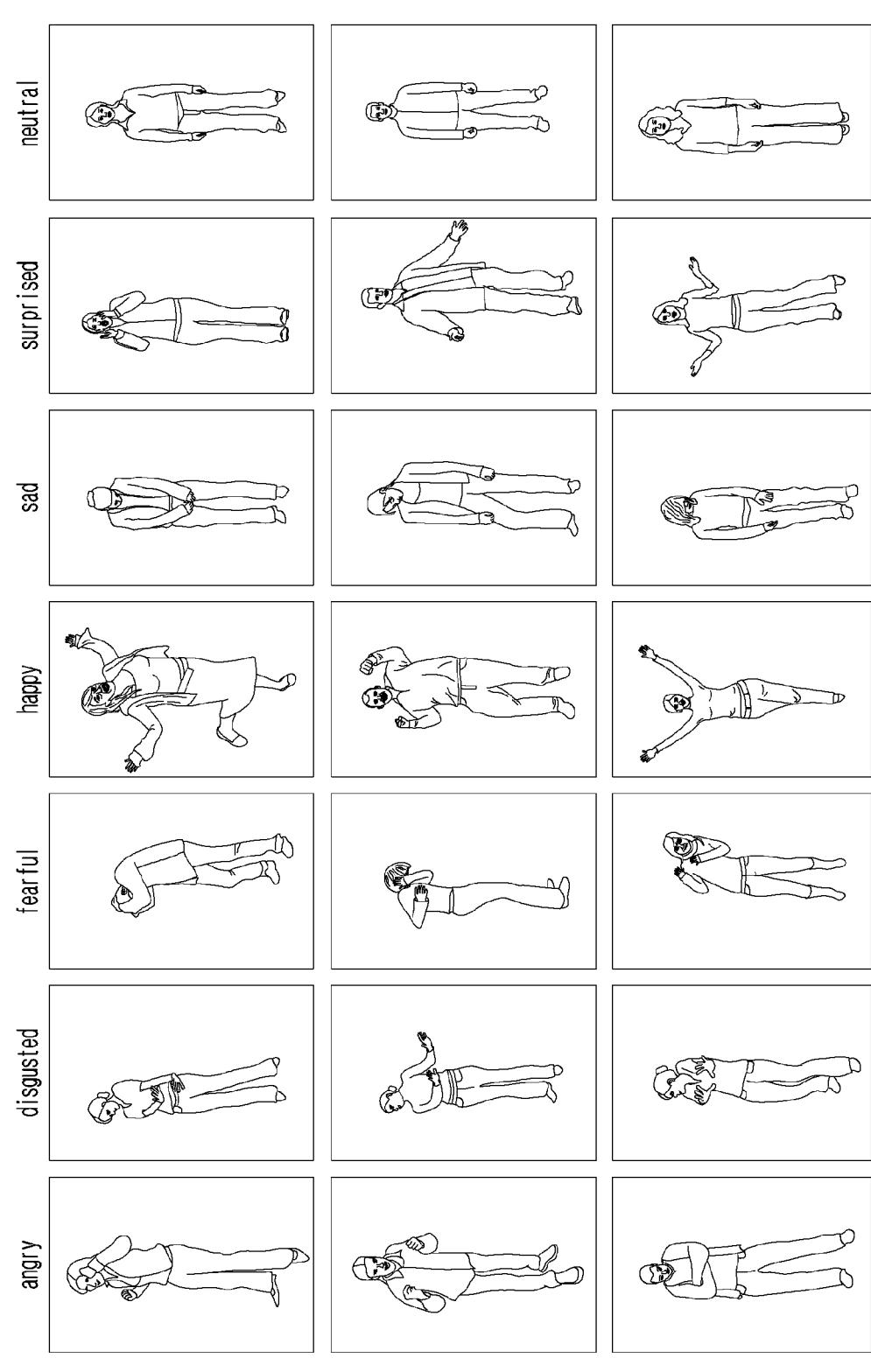

Referring to FIG. 16C, the digital twin is used to provide posture personalization based on the predicted emotion of the user in the virtual setting. Similarly, the digital twin can be used to provide clothing preference to the user based on the predicted emotion in the virtual setting. Here, clothing preference or recommendation can be prioritized based on the predicted emotion of the user, in personal space. Further, clothing recommendation in store can be prioritized based on personality of the user.

Figure 16D:
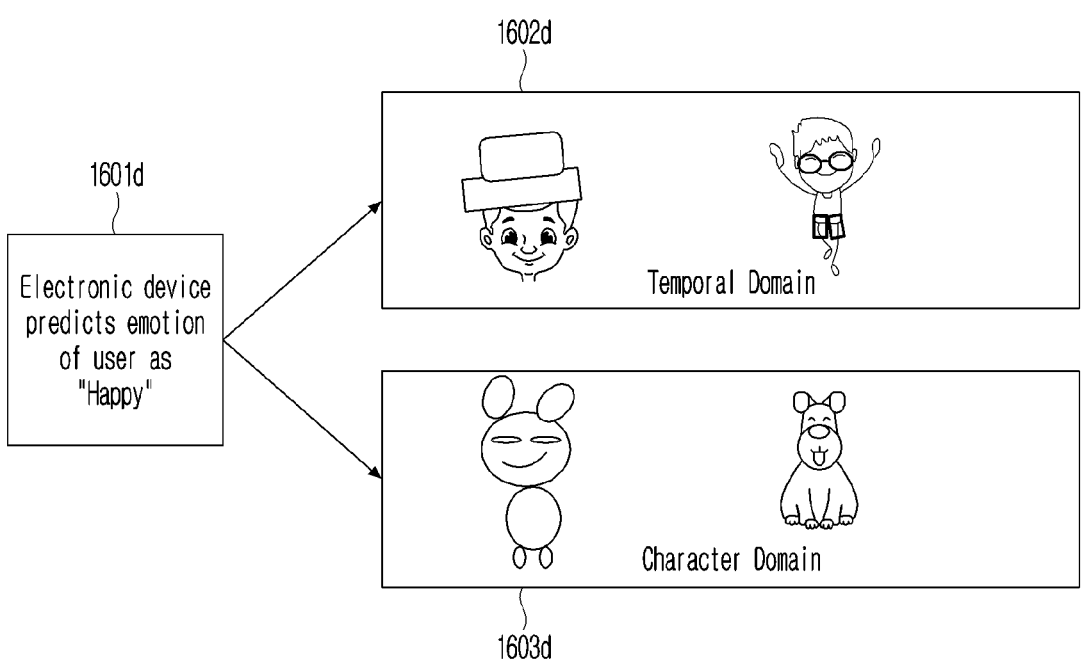

Referring to FIG. 16D, the digital twin can be used for emotion replication across virtual environments. Consider at operation 1601*d*, the predicted emotion of the user is "Happy". Then at operation 1602*d*, the predicted emotion of the user is replicated across temporal domain (i.e., the emotional behavior based on a particular age range). At operation 1603*d*, the predicted emotion of the user is replicated across character domain (i.e., emotional behavior based on character chosen by the user such as for example a dog, a human caricature, etc.).

Figure 17A:
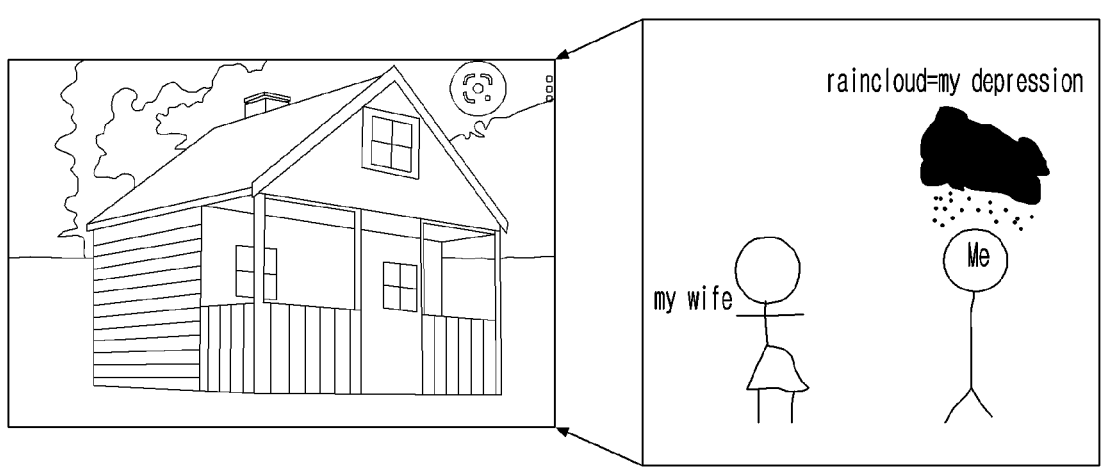
FIG. 17A illustrates an example environment modelling scenario, according to the embodiments herein.

FIG. 17A illustrates an example environment modelling scenario, according to the embodiments described herein. Referring to FIG. 17A, the example provides a scenario of the environment modelling where the environment changes with the emotion of the user in the Metaverse. Here, consider that the user suffers depression when encountered with rain and cloudy weather. Therefore, the proposed method takes into consideration the environment of the user and house features are modified based on the emotions of the user (e.g., light, exterior, interiors etc.). Further, environment modification near an avatar's area can also be provided based on the emotion of the user.

Figure 17B:
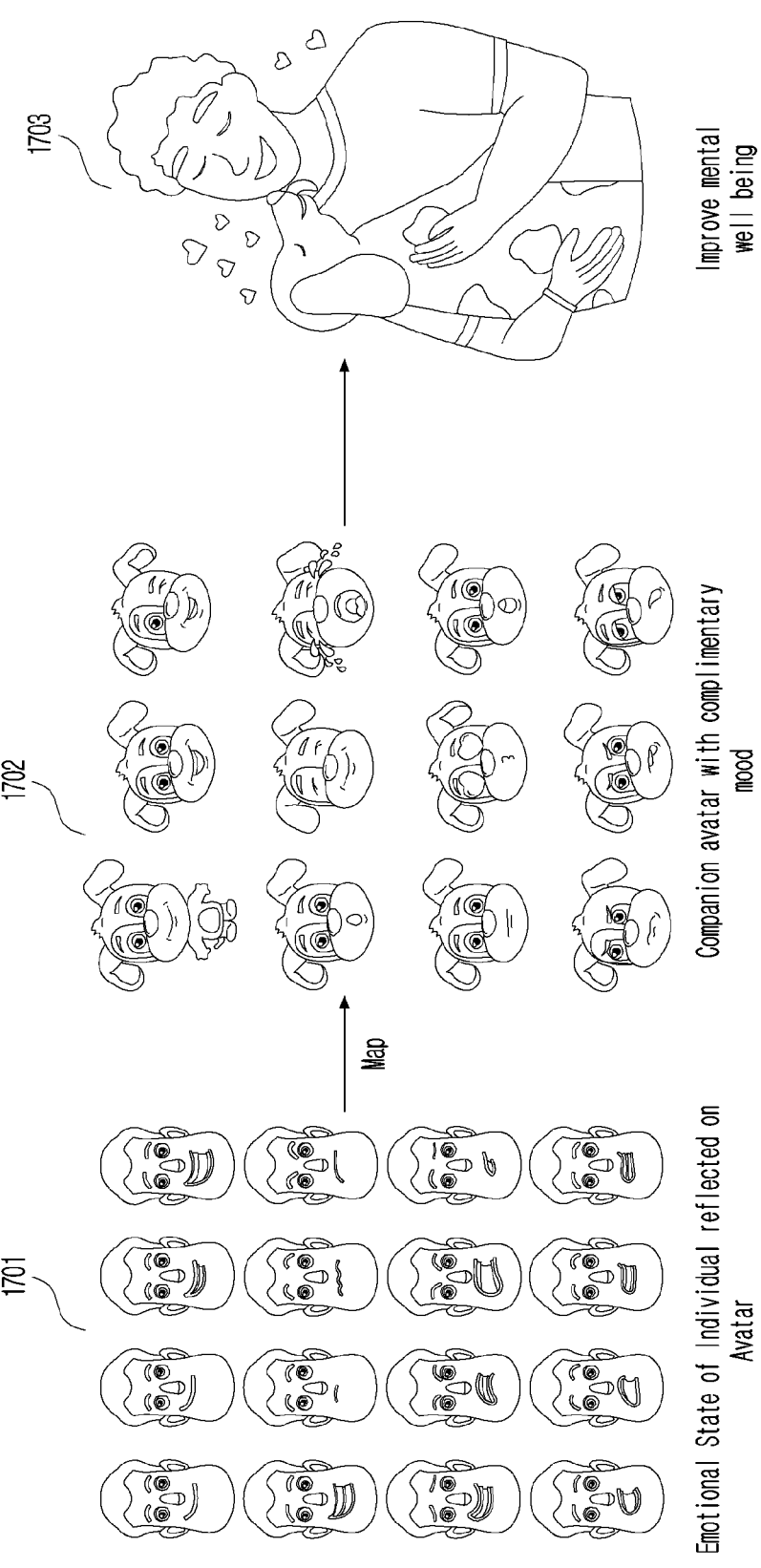
FIG. 17B illustrates another example environment modelling scenario, according to the embodiments herein.

FIG. 17B illustrates another example environment modelling scenario, according to the embodiments herein.

Referring to FIG. 17B, the example provides a scenario of companion character modelling for providing emotional support to the user. Here, the companions can be any objects such as for example but not limited to animals, humans/friends, birds, a robot, etc. In general, animals are believed to provide joy and companionship to humans. The animals can also provide emotional support to the humans with mental health concerns. At operation 1701, the various emotions of the user predicted by the electronic device 100 are used to determine virtual companions such as a dog (operation 1702) which are complimentary with each of the emotions of the user. The virtual companions are used for the user to improve mental wellbeing and boost positive emotions in virtual environments (operation 1703).

Further, the proposed method for predicting the emotions of the user based on the state of the electronic device 100, the life pattern of the user and the environmental factors can be used to provide emotion security to the users in scenarios like conversing with the emotion in a virtual environment.

One such technique of providing emotion security includes emotion masking. When the user is conversing in a virtual environment, various user personality parameters such as pitch, tone and lingo of the user can be modified and presented in the virtual environment as per the emotional state of the user.

Another example of providing the emotion security to the user includes selectively displaying or hiding the emotion of the user based on the individual with whom the user is interacting in the virtual environment. Consider that the user is in a meeting then the emotions of the user can be hidden from some attendees or different emotions can be shown to friends, colleagues, family, etc. For example, consider a situation where a user is attending an office meeting. In this situation, the Avatar may express emotion in a different way in formal and informal setting such as, for example, toned down emotion in the formal setting and raw emotion in the informal setting.

Another scenario is providing emotion security in the virtual environment. Distance alone cannot solve the problem. There are other aspects such as detecting explicit contents like nudity and vulgar gestures and censor them to prevent the user from emotional stress. Further, the proposed method can also be used to provide emotion privacy by revealing the emotion based on environmental vulnerabilities, etc. This is especially useful when children are involved as children are sensitive to strong emotions (such as for example, child-safe content).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope of the embodiments as described herein.

What is claimed is:

1. A method of operating an electronic device, the method comprising:

receiving, by the electronic device, a user context, a device context and an environment context, wherein the user context, the device context, and the environment context are collected by at least one of the electronic device and at least one of one or more other electronic devices connected to the electronic device;

determining, by the electronic device, a combined representation of the user context, the device context and the environment context;

determining, by the electronic device, a plurality of user characteristics based on the combined representation of the user context, the device context and the environment context;

predicting, by the electronic device, an emotion of a user based on the plurality of user characteristics and the combined representation of the user context, the device context, the environment context; and personalizing, by the electronic device, content on the electronic device and on at least one of the one or more other electronic devices based on the predicted emotion of the user, wherein the personalizing the content comprises at least one of:

adjusting a speed of an animation on a display of the electronic device;

adjusting a duration of a security lock on the display of the electronic device; or adjusting a color palette of a user interface of the electronic device, and wherein the determining, by the electronic device, the combined representation of the user context, the device context and the environment context comprises:

determining a plurality of features associated with the user from the user context, the device context and the environment context;

segregating the plurality of features associated with the user into a plurality of categories corresponding to a specific duration of time;

generating, using encoding, at least one vector representation for each of the plurality of categories; and determining the combined representation of the user context, the device context and the environment context based on the at least one vector representation for each of the plurality of categories.

2. The method of claim 1, further comprising:

performing, by the electronic device, based on the predicted emotion of the user, at least one of:

modifying a user experience on the electronic device and on at least one of the one or more other electronic devices, utilizing an emotional profile on the electronic device and on at least one of the one or more other electronic devices, generating at least one object for providing an emotional support to the user, providing a security function to the user in a virtual environment, and modifying at least one user parameter in the virtual environment.

3. The method of claim 1, further comprising:

determining, by the electronic device, at least one of: a consumption of content by the user, abnormal usage pattern on the electronic device or on at least one of the one or more other electronic devices, a recurrence activity performed on the electronic device or on at least one of the one or more other electronic devices by the user, and a time duration spent by the user on the electronic device or on at least one of the one or more other electronic devices; and determining, by the electronic device, a quality of the predicted emotion of the user, wherein the quality of the predicted emotion is a positive emotion or a negative emotion.

4. The method of claim 1, wherein the determining, by the electronic device, the plurality of user characteristics based on the combined representation of the user context, the device context and the environment context comprises:

providing, by the electronic device, the combined representation of the user context, the device context and the environment context to a first network and a plurality of intermediate models; and determining, by the electronic device, the plurality of user characteristics.

5. The method of claim 4, further comprising:

predicting, by the electronic device, a first set of intermediate emotions based on the plurality of user characteristics and the combined representation of the user context, the device context and the environment context.

6. The method of claim 4, further comprising:

providing, by the electronic device, the combined representation of the user context, the device context and the environment context to a second network and a third network;

determining, by the electronic device, a local graph emotion prediction from the second network and a global node prediction from the third network;

combining, by the electronic device, the local graph emotion prediction and the global node prediction based on a specific weight; and predicting, by the electronic device, a second set of intermediate emotions.

7. The method of claim 1, wherein the predicting, by the electronic device, the emotion of the user based on the combined representation of the user context, the device context, the environment context and the plurality of user characteristics comprises:

receiving, by at least one second model of the electronic device, a first set of intermediate emotions and a second set of intermediate emotions;

receiving, by the at least one second model of the electronic device, a categorical clustering map;

performing, by the at least one second model of the electronic device, an ensembling technique on the first set of intermediate emotions and the second set of intermediate emotions based on the categorical clustering map; and predicting, by the electronic device, the emotion of the user.

8. The method of claim 1, wherein the plurality of user characteristics is determined using at least one first model and wherein the emotion of the user is predicted using at least one second model.

9. An electronic device comprising:

at least one memory configured to store at least one instruction;

at least one processor in communication with the at least one memory and configured to execute the at least one instruction; and a communicator in communication with the at least one memory and the at least one processor, wherein the at least one instruction, when executed by the at least one processor, causes the electronic device to:

receive a user context, a device context and an environment context, wherein the user context, the device context, and the environment context are collected by at least one of the electronic device and at least one of one or more other electronic devices connected to the electronic device;

determine a combined representation of the user context, the device context and the environment context by:

determining a plurality of features associated with a user from the user context, the device context and the environment context, segregating the plurality of features associated with the user into a plurality of categories corresponding to a specific duration of time, generating at least one vector representation for each of the plurality of categories, and determining the combined representation of the user context, the device context and the environment context based on the at least one vector representation for each of the plurality of categories;

determine a plurality of user characteristics based on the combined representation of the user context, the device context and the environment context;

predict an emotion of the user based on the plurality of user characteristics and the combined representation of the user context, the device context, the environment context; and personalize content on the electronic device and on at least one of the one or more other electronic devices based on the predicted emotion of the user by performing at least one of:

adjusting a speed of an animation on a display of the electronic device, adjusting a duration of a security lock on the display of the electronic device, or adjusting a color palette of a user interface of the electronic device.

10. The electronic device of claim 9, wherein the at least one instruction, when executed by the at least one processor, further causes the electronic device to perform, based on the predicted emotion of the user, at least one of:

modifying a user experience on the electronic device and on at least one of the one or more other electronic devices, utilizing an emotional profile on the electronic device and on at least one of the one or more other electronic devices, generating at least one object for providing an emotional support to the user, providing a security function to the user in a virtual environment, and modifying at least one user parameter in the virtual environment.

11. The electronic device of claim 9, wherein the at least one instruction, when executed by the at least one processor, further causes the electronic device to:

determine at least one of: a consumption of content by the user, abnormal usage pattern on the electronic device or on at least one of the one or more other electronic devices, a recurrence activity performed on the electronic device or on at least one of the one or more other electronic devices by the user, and a time duration spent by the user on the electronic device or on at least one of the one or more other electronic devices; and determine a quality of the predicted emotion of the user, wherein the quality of the predicted emotion is a positive emotion or a negative emotion.

12. The electronic device of claim 9, wherein the at least one instruction, when executed by the at least one processor, further causes the electronic device to:

determine the plurality of user characteristics based on the combined representation of the user context, the device context and the environment context by providing the combined representation of the user context, the device context and the environment context to a first network and a plurality of intermediate models.

13. The electronic device of claim 12, wherein the at least one instruction, when executed by the at least one processor, further causes the electronic device to:

predict a first set of intermediate emotions based on the plurality of user characteristics and the combined representation of the user context, the device context and the environment context.

14. The electronic device of claim 12, wherein the at least one instruction, when executed by the at least one processor, further causes the electronic device to:

provide the combined representation of the user context, the device context and the environment context to a second network and a third network;

determine a local graph emotion prediction from the second network and a global node prediction from the third network;

combine the local graph emotion prediction and the global node prediction based on a specific weight; and predict a second set of intermediate emotions.

15. The electronic device of claim 9, wherein the at least one instruction, when executed by the at least one processor, further causes the electronic device to predict the emotion of the user based on the plurality of user characteristics and the combined representation of the user context, the device context, the environment context by:

receiving, by at least one second model of the electronic device, a first set of intermediate emotions and a second set of intermediate emotions;

receiving, by the at least one second model of the electronic device, a categorical clustering map;

performing, by the at least one second model of the electronic device, an ensembling technique on the first set of intermediate emotions and the second set of intermediate emotions based on the categorical clustering map; and predicting, by the electronic device, the emotion of the user.

16. The electronic device of claim 9, wherein the at least one instruction, when executed by the at least one processor, further causes the electronic device to:

determine a plurality of user characteristics based on the combined representation of the user context, the device context and the environment context using at least one first model, and predict the emotion of the user using at least one second model.

* * * * *